(12) United States Patent
Fahim et al.

(10) Patent No.: US 11,179,200 B2
(45) Date of Patent: Nov. 23, 2021

(54) AUGMENTED REALITY SOLUTION TO DISRUPT, TRANSFORM AND ENHANCE CARDIOVASCULAR SURGICAL AND/OR PROCEDURAL MAPPING NAVIGATION AND DIAGNOSTICS

(71) Applicant: Medtronic, Inc., Minneapolis, MN (US)

(72) Inventors: Mina S. Fahim, New Brighton, MN (US); Peter N. Braido, Linwood, MN (US); Ross D. Hinrichsen, Minneapolis, MN (US); Jeffrey J. Jannicke, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 642 days.

(21) Appl. No.: 15/843,062

(22) Filed: Dec. 15, 2017

(65) Prior Publication Data
US 2019/0183576 A1    Jun. 20, 2019

(51) Int. Cl.
*A61B 34/10* (2016.01)
*A61B 90/00* (2016.01)
(Continued)

(52) U.S. Cl.
CPC ............. *A61B 34/10* (2016.02); *A61B 18/12* (2013.01); *A61B 34/20* (2016.02); *A61B 34/25* (2016.02);
(Continued)

(58) Field of Classification Search
CPC ...... A61N 1/3627; A61B 90/36; A61B 34/20; A61B 34/10; A61B 34/25; A61B 18/12;
(Continued)

(56) References Cited

U.S. PATENT DOCUMENTS

| | | | |
|---|---|---|---|
| 2011/0152712 A1* | 6/2011 | Cao | A61B 5/6852 600/547 |
| 2013/0267835 A1* | 10/2013 | Edwards | A61B 5/063 600/424 |

(Continued)

FOREIGN PATENT DOCUMENTS

WO    2017165301 A1    9/2017

OTHER PUBLICATIONS

International Search Report and Written Opinion dated Mar. 14, 2019, for corresponding International Application No. PCT/US2018/063597; International Filing Date: Dec. 3, 2018 consisting of 10 pages.

*Primary Examiner* — Bo Joseph Peng
(74) *Attorney, Agent, or Firm* — Christopher & Weisberg, P.A.

(57) ABSTRACT

An augmented reality system includes an augmented reality display system; and processing circuitry in communication with the augmented reality display system. The processing circuity configured to receive, from a mapping system, data associated with a subject's anatomical feature; receive, from a navigation system, an indication of a position of a treatment device within the subject's anatomical feature; and display, via the augmented reality display system, a virtual organ object and at least one of the data associated with the subject's anatomical feature and the indication of the position of the treatment device within the subject's anatomical feature overlaying a real-world environment viewable by a user via the augmented reality display system.

7 Claims, 12 Drawing Sheets

(51) Int. Cl.
    *A61B 18/12*    (2006.01)
    *A61B 34/20*    (2016.01)
    *A61B 34/00*    (2016.01)
    *A61N 1/362*    (2006.01)
    *G06T 19/00*    (2011.01)
(52) U.S. Cl.
    CPC ............ *A61B 90/36* (2016.02); *A61N 1/3627* (2013.01); *G06T 19/006* (2013.01); *A61B 2034/102* (2016.02); *A61B 2034/254* (2016.02); *A61B 2090/365* (2016.02)
(58) Field of Classification Search
    CPC ........ A61B 2034/254; A61B 2034/102; G06T 19/006; G10H 2210/18; G05B 2219/39451; G05B 2219/39449; G06K 9/00671
    See application file for complete search history.

(56) References Cited

U.S. PATENT DOCUMENTS

| | | | |
|---|---|---|---|
| 2014/0276709 A1* | 9/2014 | Wittenberger | A61B 18/1492 606/23 |
| 2015/0320515 A1* | 11/2015 | Edwards | A61B 5/066 600/389 |
| 2016/0022375 A1* | 1/2016 | Blake | A61B 5/6844 600/424 |
| 2016/0249989 A1* | 9/2016 | Devam | G09B 23/285 345/633 |
| 2017/0035499 A1 | 2/2017 | Stewart et al. | |
| 2017/0186157 A1* | 6/2017 | Boettger | G06T 7/70 |
| 2017/0312031 A1 | 11/2017 | Amanatullah et al. | |
| 2017/0325733 A1* | 11/2017 | Hettrick | G06F 19/3481 |

* cited by examiner

AUGMENTED REALITY SOLUTION TO DISRUPT, TRANSFORM AND ENHANCE CARDIOVASCULAR SURGICAL AND/OR PROCEDURAL MAPPING NAVIGATION AND DIAGNOSTICS

CROSS-REFERENCE TO RELATED APPLICATION n/a

STATEMENT REGARDING FEDERALLY SPONSORED RESEARCH OR DEVELOPMENT n/a

TECHNICAL FIELD

The present invention relates to a method and system for providing an augmented/mixed reality solution to enhance cardiovascular surgical and/or procedural mapping, navigation, and diagnostics.

BACKGROUND

Cardiac arrhythmias, such as ventricular tachycardia and atrial fibrillation, present in the heart disrupt normal rhythm and cardiac efficiency. These arrhythmias can be treated using ablation techniques such as radiofrequency (RF), ultrasound, microwave, pulsed electric field, cryoablation, and other forms of ablation. In the case of ablation techniques that involve the delivery of electrical therapy, a catheter can be used to deliver ablation energy, or direct visualization with surgical ablation tools may be used.

For example, procedures such as pulmonary vein isolation (PVI) are commonly used to treat atrial fibrillation. This procedure may involve the use of a cryogenic device, such as a cryoballoon catheter, which is positioned at the ostium of a pulmonary vein (PV) such that any blood flow exiting the PV into the left atrium (LA) is completely blocked. In some procedures, once in position, the cryogenic device may be activated for a sufficient duration to create a desired lesion within myocardial tissue at the PV-LA junction, such as a PV ostium. If a cryoballoon is used as the treatment element of the cryogenic device, the cryoballoon is typically inflated using a fluid or gas coolant, enabling the balloon to create a circumferential lesion about the ostium and/or antrum of the PV to disrupt aberrant electrical signals exiting the PV.

The success of this procedure depends largely on the quality of the lesion(s) created during the procedure and whether the cryoballoon has completely occluded the PV. For example, a complete circumferential lesion is produced only when the cryoballoon has completely occluded the PV. Incomplete occlusion allows blood to flow from the PV being treated, past the cryoballoon, and into the left atrium of the heart. This flow of warm blood may prevent the cryoballoon from reaching temperatures low enough to create permanent lesions in the target tissue. The creation of reversible lesions may not be sufficient to achieve electrical isolation and, as a result, atrial fibrillation may be likely to reoccur. Additionally, even if the PV is completely occluded, suboptimal operation of the cryoablation system may result in cryoballoon temperatures that are not low enough, or not applied for a sufficient amount of time, to create permanent lesions in the target tissue.

Current methods of assessing or monitoring PV occlusion include fluoroscopic imaging of radiopaque contrast medium injected from the device into the PV. If the device, such as a cryoballoon catheter, has not completely occluded the PV ostium, some of the contrast medium may flow from the PV into the left atrium. In that case, the device may be repositioned and more contrast medium injected into the PV. Unfortunately, this method exposes the patient to potentially large doses of contrast medium and exposes the patient, physician, and support staff to radiation. Also, fluoroscopy imaging techniques to assess PV occlusion require the use of x-rays that are known to be harmful to patients and necessitate physicians wearing heavy lead suits, which can inhibit the physician physically during the procedure, and, over time, may result in physical, orthopedic stress for the physician.

Alternatively, pressure measurement distal to the occlusion site can be used to assess occlusion prior to initiating the coolant injection. Other methods may involve the use of temperature sensors to determine the temperature within the cryoballoon and to correlate the measured temperature to a predicted thickness of ice created in tissue that is in contact with the cryoballoon. Yet other methods include, for example, a pressure wedge, cooled saline, impedance, Doppler echo, etc. However, data from these types of sensor readings typically involve conventional monitors (e.g., desktop monitors). In addition, multiple operators and monitors are often required, which can increase the cost, complexity, and inefficiency of the workflow for the procedure. In other words, existing systems require physicians to look away from the patient during steering and manipulation of catheters to view procedural diagnostic data and to ensure correct anatomical navigation. This can lead to a higher risk of damage to adjacent anatomical features such as the phrenic and vagal plexus nerves, adjacent coronary arteries, or the esophageal wall. Some physicians may elect to forego the use of conventional monitors, or may not view the information on the monitors as frequently as they would prefer in order to avoid looking constantly looking away from the patient during the procedure.

In addition to PVI, ablation of adjacent anatomical structures such as the posterior wall, left atrial appendage, roof of the left atrium and mitral isthmus line may be conducted to ensure complete electrical isolation of the left atrium. Confidently visualizing and navigating to these anatomical structures is important for confident ablation without damage to adjacent structures. Such ablations can be achieved using either a balloon such as the cryoballoon, RF balloon, laser balloon, etc. Additionally, these linear lesions can be created using a linear catheter such as Arctic Line cryo linear catheter, RF linear catheter, a laser linear catheter or point by point RF or cryo ablation.

A clear line of vision to target anatomies while conducting various types of invasive as well as minimally invasive medical procedures can greatly enhance the safety and efficacy of such procedures. Due to the technical limitations of current systems and physician caution while trying to minimize the risk of complications, visualization of target anatomy during a procedure can be limited. In addition, the cost of current navigation and mapping systems are very expensive, which limits the accessibility to these systems, for procedures, as well as, for on-site and remote training (e.g., telementoring). Procedural diagnostics play an important role in assisting physicians with administering therapies. Such diagnostic information (e.g., sensor data, mapping, navigation data, biometrics, disease state data, treatment device positioning indicators, feedback on therapy effectiveness, etc.) can greatly contribute to the quality of patient outcomes. Unfortunately, this diagnostic information is not readily accessible and requires multiple monitors and systems.

Augmented reality devices blend computer-generated information with the user's view of the physical world, i.e., the real world. Stated another way, augmented reality devices augment computer-displayed information to the user's view of the real-world environment in order to enhance situational awareness of the user within the physical world with the computer-displayed information. However, existing augmented reality devices are rather limited in their use and have been primarily limited to personal use, rather than for medical imaging and procedures.

Accordingly, in light of the above limitations, it would be desirable to provide systems, devices, and methods for providing an augmented/mixed reality solution to enhance cardiovascular procedural and/or surgical mapping, navigation, and diagnostics.

SUMMARY

The present invention advantageously provides a method and system for providing an augmented reality solution to enhance cardiovascular surgical mapping, navigation and procedural diagnostics. In particular, one aspect of the present invention includes an augmented reality system with an augmented reality display system; and processing circuitry in communication with the augmented reality display system. The processing circuitry is configured to receive, from a mapping system, data associated with a subject's anatomical feature; receive, from a navigation system, an indication of a position of a treatment device within the subject's anatomical feature; and display, via the augmented reality display system, a virtual organ object and at least one of the data associated with the subject's anatomical feature and the indication of the position of the treatment device within the subject's anatomical feature overlaying a real-world environment viewable by a user via the augmented reality display system.

In this and other aspects, embodiments of the present invention include the virtual organ object being based on a three-dimensional model of the subject's anatomical feature, the subject's anatomical feature including at least one of at least a portion of a heart and at least a portion of vasculature. The data includes electrogram data; and the virtual organ object, the at least one of the data associated with the subject's anatomical feature and the indication of the position of the treatment device, and the real-world environment are simultaneously viewable by a user via the augmented reality display system within a field of view of the user. Further, the navigation system is configured to continuously monitor the position of the treatment device within the subject's anatomical feature during a surgical procedure; and the processing circuitry is configured to continuously receive the monitored position from the navigation system and display an indication of the monitored position on the virtual organ object during the surgical procedure. The processing circuitry is further configured to continuously update the indication of the monitored position on the virtual organ object during the surgical procedure. The navigation system is also configured to deliver alternating current to a plurality of external electrodes and orient a plurality of current sources in at least an X plane, a Y plane, and a Z plane for determining the position of the treatment device within the subject's anatomical feature.

At least one of the navigation system and the mapping system include at least one medical sensor; and the processing circuitry is configured to receive data associated with the at least one medical sensor and display an indication of the data via the augmented reality display system. The at least one medical sensor is configured to sense an electrical parameter of the heart; and the processing circuitry is configured to display an indication of the electrical parameter via the augmented reality display system. The at least one medical sensor includes at least one of a temperature sensor, a pressure sensor, and an electrode. The processing circuitry is configured to receive, from at least one sensor, an indication of at least one of an occlusion of a pulmonary vein and a parameter associated with a lesion; and the processing circuitry is configured to display, via the augmented reality display system, the indication of the at least one of an occlusion of a pulmonary vein and a parameter associated with a lesion. The indication of the at least one of an occlusion of a pulmonary vein and a parameter associated with a lesion is based on at least one of an impedance measurement and a temperature measurement from the at least one sensor. Mesh collision between the patient anatomy virtual mesh and the virtual mesh of the ablation tool can also be used to provide feedback on quality of occlusion prior, during and after ablation.

In accordance with another aspect, a method is provided for enhancing a surgical procedure. The method includes receiving, by an augmented reality device including an augmented reality display system, data associated with a subject's anatomical feature and an indication of a position of a treatment device within the subject's anatomical feature; and displaying, via the augmented reality display system, a virtual organ object and at least one of the data and the indication of the position of the treatment device overlaying a real-world environment viewable by a user via the augmented reality display system. The receiving and displaying are performed during a surgical procedure, where the user is a surgeon and the real-world environment includes at least a portion of a body of the patient in a surgical room. The virtual organ object, at least one of the data and the indication of the position, and the at least a portion of the body of the patient are simultaneously viewable by the surgeon via the augmented reality display system during the surgical procedure.

In accordance with this aspect, in some embodiments, the virtual organ object is based on a three-dimensional model of the subject's anatomical feature, the subject's anatomical feature including at least one of at least a portion of a heart and at least a portion of vasculature. The augmented reality device continuously receives the position of the treatment device within the subject's anatomical feature during a surgical procedure, and continuously updates the indication of the position of the treatment device on the virtual organ object during the surgical procedure. The augmented reality device receive data from the at least one medical sensor and displays an indication of the data from the at least one medical sensor via the augmented reality display system. An indication of at least one of an occlusion of a pulmonary vein and a parameter associated with a lesion is received by the augmented reality device from at least one sensor; and the indication is displayed via the augmented reality display system.

In accordance with yet another aspect, a method is provided for enhancing a surgical procedure. The method includes receiving, by an augmented reality device including an augmented reality display system, an indication of a position of a treatment device within a subject's anatomical feature; displaying, via the augmented reality display system, a virtual organ object and the indication of the position of the treatment device within the subject's anatomical feature overlaying a real-world environment viewable by a user via the augmented reality display system; and continuously updating the indication of the position of the treatment device on the virtual organ object during the surgical procedure.

In accordance with this aspect, in some embodiments, the virtual organ object is based on a three-dimensional model of the subject's anatomical feature, the subject's anatomical feature including at least one of at least a portion of a heart and at least a portion of vasculature. Electrogram data associated with the subject's anatomical feature is received by the augmented reality device; and the virtual organ object and the electrogram data are displayed, via the augmented reality display system, overlaying the real-world environment viewable by the user via the augmented reality display system.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

The present disclosure describes systems, devices, and methods for providing an augmented reality solution to enhance cardiovascular surgical mapping, navigation, and procedural diagnostics. Most commonly performed surgical procedures, such as those for the treatment of cardiac conditions, present challenges to the physician. For example, for heart failure treatment procedures requiring trans-venous access, these challenges include inability to visualize branching of a venous structure during positioning of a treatment device (for example, when performing coronary sinus cannulation) and difficulty of and real-time assessment of cardiac lead placement. Additionally, for heart failure treatment procedures requiring sub-sternal access, these challenges include the requirement of a full thoracotomy, rib removal, and/or lung deflation, and the unavailability of tools suitable for navigating to the lead delivery location. The systems, devices, and methods described herein not only overcome these procedural challenges, but also provide additional benefits, such as the meaningful integration of information from a variety of biometric, treatment, navigational, and diagnostic systems into a single user-friendly system, and facilitation of minimally invasive and non-invasive surgery, device positioning and placement, pre-procedural planning to evaluate disease state (e.g., annulus eccentricity, level of calcification, cardiac output, or the like), and others.

Before describing in detail exemplary embodiments of the present disclosure, it should be noted that the terms "augmented reality" and "mixed reality" are used interchangeably and are intended to indicate devices, methods, and/or systems in which data, information, virtual images or objects, graphics, and the like, or other sensor, or computer-generated, actionable decision-making information are provided to the observer by a source, such as a display source (e.g., wearable devices or hologram projectors, etc.), within a real-world environment simultaneously observable by the observer. In some embodiments of the present disclosure described herein, "mixed reality" may further indicate devices, methods, and/or systems in which real-time data from one or more information sources is communicated, transmitted, streamed, and/or presented/rendered to the observer within the real-world environment. In yet other embodiments of the present disclosure, "mixed reality" and "augmented reality" may further indicate devices, methods, and/or systems in which the computer-generated information being presented/rendered to the observer as interacting with, or otherwise being tied to at least a portion of the real-world environment.

Figure 1:
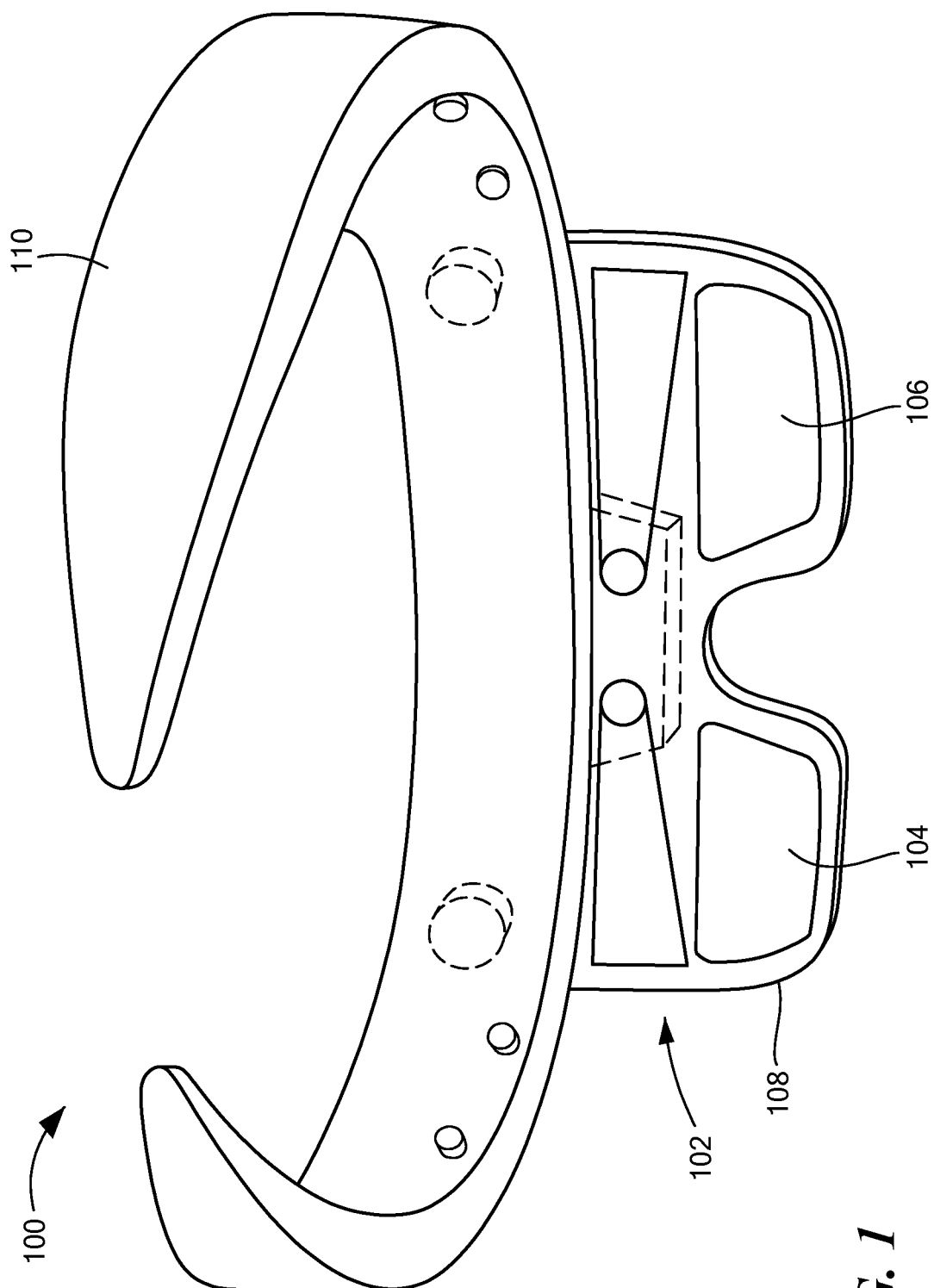
FIG. 1 illustrates a rear perspective view an exemplary augmented reality device in accordance with the principles of the present disclosure.
Figure 3:
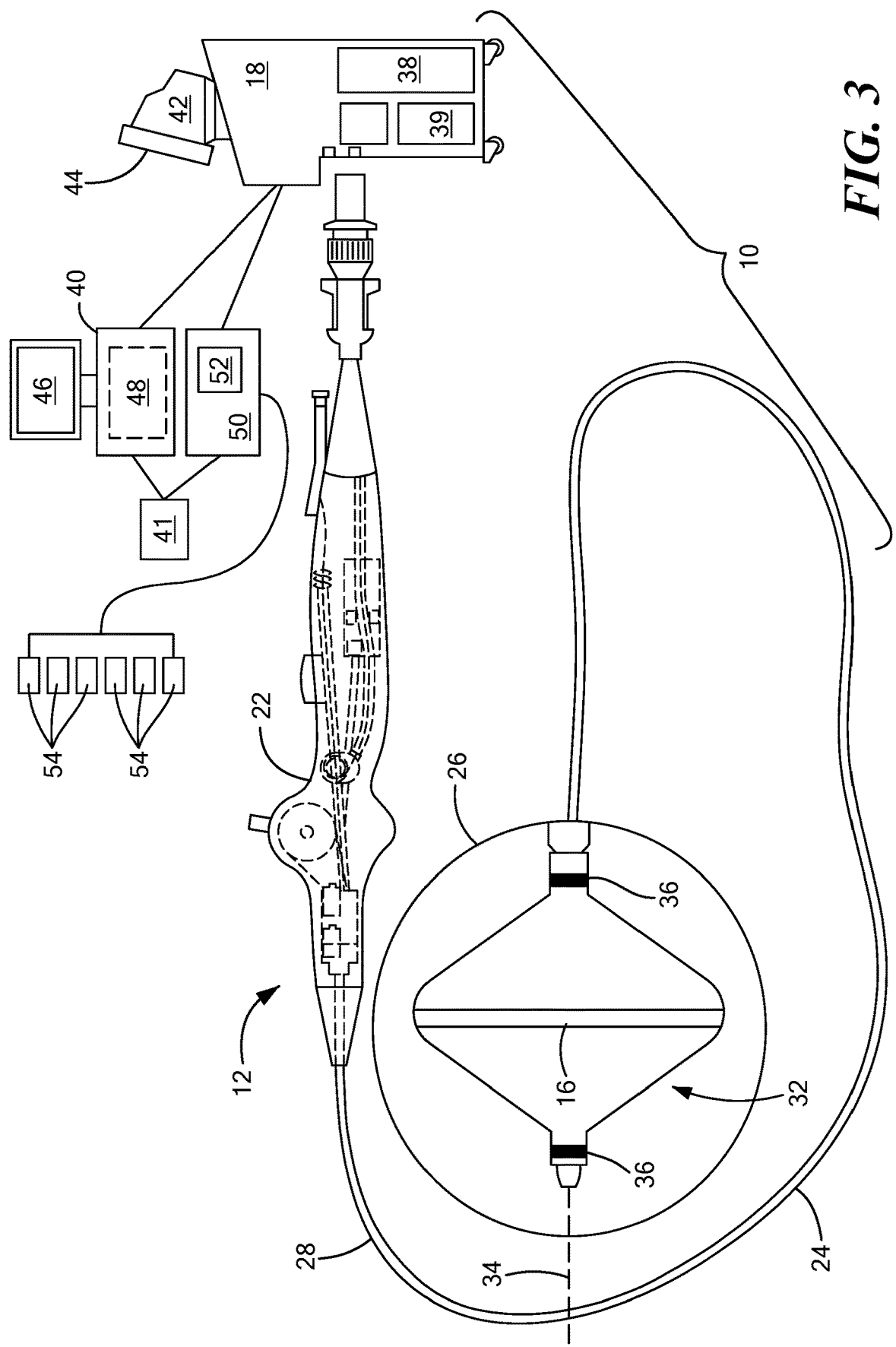
FIG. 3 illustrates an exemplary medical system in accordance with the present disclosure.
Figure 5:
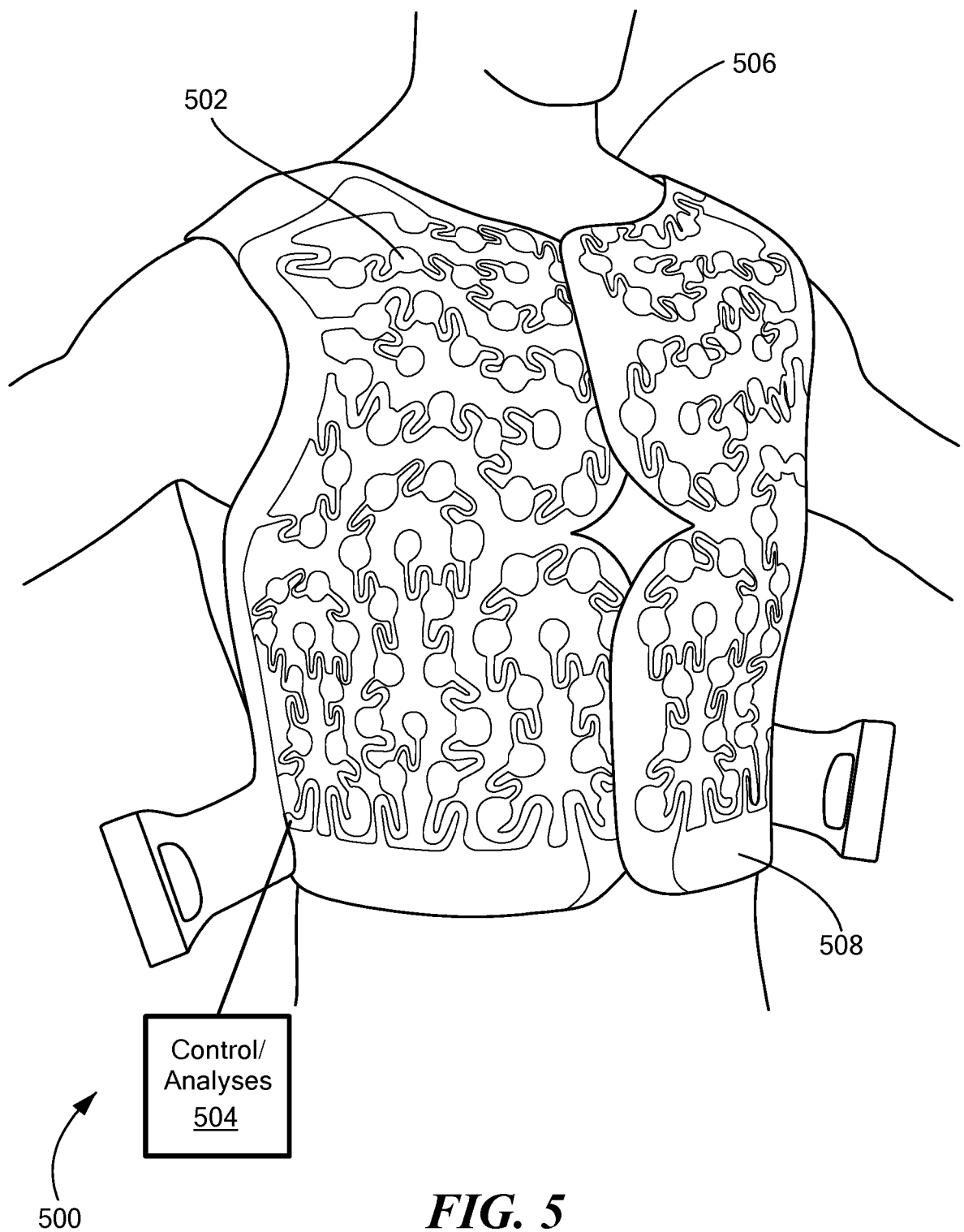
FIG. 5 illustrates an exemplary mapping system at least partially disposed on a patient in accordance with an embodiment of the present disclosure.

Referring now to the drawing figures in which like reference designations refer to like elements, an embodiment of an augmented reality device in accordance with principles of the present invention is shown in FIG. 1 and generally designated as "100." FIGS. 3 and 5 show an embodiment of a medical system 10 and a mapping system 500, respectively, in communication with the augmented reality device 100.

The following description will begin with an introduction of the various exemplary components of the augmented reality device 100, and the medical system 10 and mapping system 500, followed by a description of an exemplary method of using and/or implementing the devices and systems 100, 10, 500 in accordance with principles of the present disclosure.

Augmented Reality Device

The exemplary augmented reality device 100 is shown in FIG. 1 as a wearable augmented reality device in the form of eyeglasses 102. The eyeglasses 102 include a pair of lenses 104, 106 and a frame 108 with a head support member 110 extending therefrom.

The head support member 110 is configured to support the augmented reality device 100 on a head of the wearer/user. The exemplary head support member 110 is shown in the form of a head band; however, alternative embodiments may be in the form of, for example, a pair of side arms configured to rest of the wearer's ears, as with traditional eyeglasses. The head support member 110, or another portion of the augmented reality device 100, may be adapted as an augmented reality device housing, for housing the augmented reality device electrical and/or optical components, such as, for example, processing circuitry, sensors, cameras, network interfaces, and like, as will be described in more detail below with reference to the block diagram of FIG. 2. An alternative embodiment may be in the form of contact lenses which wirelessly communicate and display the information being generated from the sub-systems to construct a mixed reality environment. An alternative embodiment may use spatial computing to project digital information into the physical world using cameras, mirrors, light refractors and stages. This would allow the display and integration of information from multiple sources without the need for the user to wear anything on their head or in their eyes.

The frame 108 and the head support member 110 can be formed of a solid rigid polymer, plastic, and/or metal structure, or can be formed as a hollow structure of similar material to allow for wiring and interconnection of internal electrical components throughout the eyeglasses 102.

The lenses 104, 106 can be sufficiently transparent to allow the user to see through the lenses 104, 106 as is traditionally provided for non-computing eyeglasses. Stated another way, the lenses 104, 106 may be considered see-through lenses 104, 106. In some embodiments, the lenses 104, 106 may be prescription lenses. In other embodiments, the lenses 104, 106 may be slightly tinted. Although, FIG. 1 shows two lenses 104, 106, it is understood that the augmented reality device 100 may include one lens or more than two lenses 104, 106.

Figure 2:
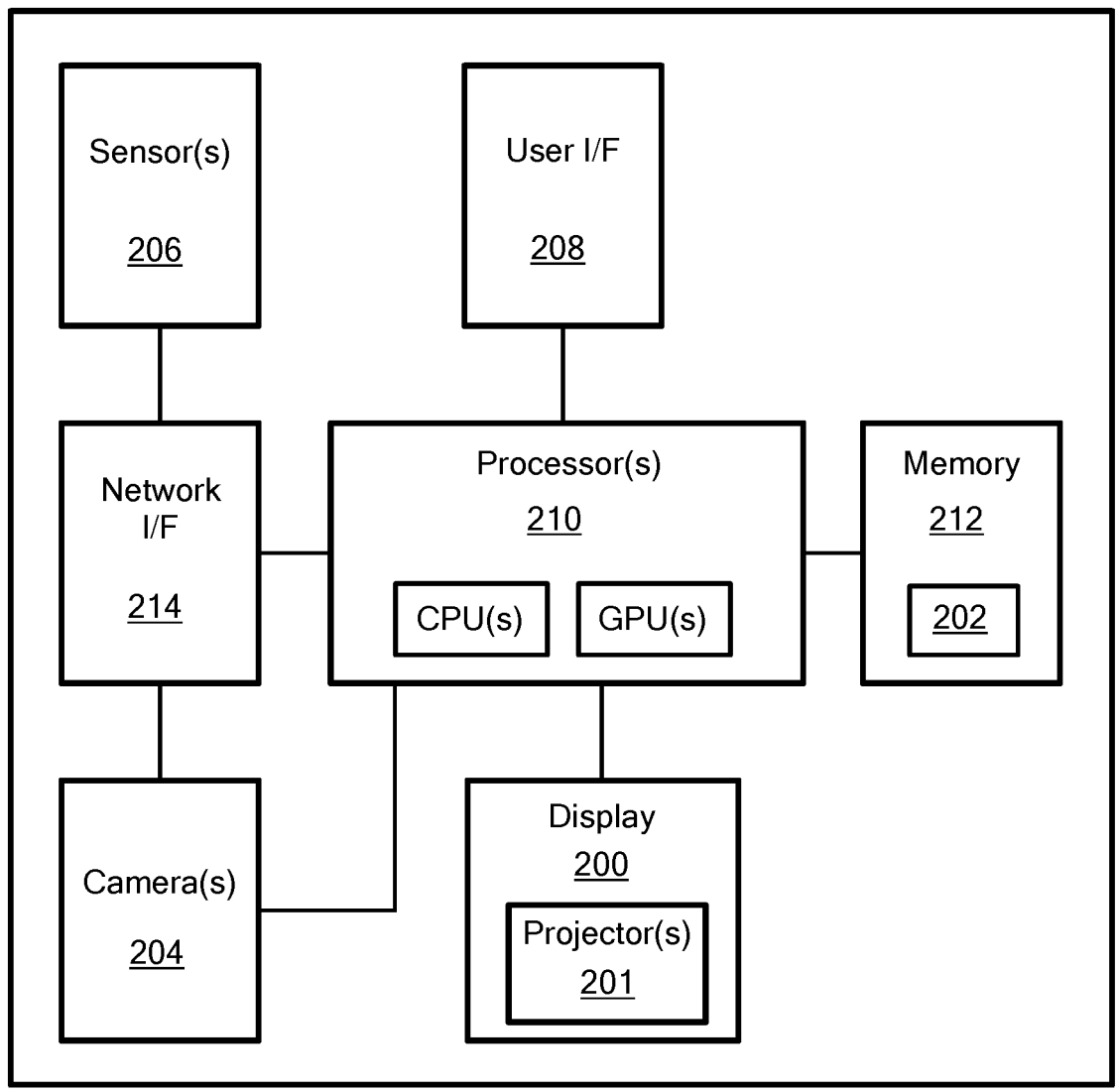
FIG. 2 illustrates a block diagram view of components of the augmented reality device of FIG. 1, in accordance with embodiments of the present disclosure.

Referring now primarily to FIG. 2, with brief reference to FIG. 1, the augmented reality device 100 can include computing components and optical components housed within the head support member 110, or otherwise supported by or included within the augmented reality device 100. The computing components and optical components may be coupled to the frame 108 and/or may be housed within the head support member 110. It is understood that any one of or a multitude of the computing and optical components may be provided on other parts of the eyeglasses 102 or can be remotely positioned, being in wireless or wired communication via a communication link with the eyeglasses 102.

Although the exemplary augmented reality device depicted in FIG. 1 is shown as a wearable augmented reality device, it is contemplated that some embodiments of the present disclosure may also be implemented in non-wearable augmented reality devices or systems.

FIG. 2 shows an example block diagram of exemplary components of the augmented reality device 100. The exemplary augmented reality device 100 may include a display system 200, a cardiac augmented reality module 202, a camera 204, a sensor 206, a user input interface 208, a processor 210, memory 212, and a network interface 214.

The display system 200 may include a micro display that may be disposed in close proximity to the wearer's eye when worn. The micro display may be disposed between the lenses 104, 106 and the wearer's eye. The micro display may be a transparent or a semi-transparent display. The micro display can be a matrix display, such as a light emitting diode (LED) display, a liquid crystal display (LCD), and the like. It is understood that any suitable display may be used in embodiments of the present disclosure provided that it allows the eyeglass wearer or user to view images as virtual objects (e.g., holograms) augmenting the wearer's (or user's) view of the physical/real-world environment viewable via the display system 200 by, for example, both the real and virtual world being viewable through the lenses 104, 106. A display driver may provide an interface between the processor 210 and the display system 200, driving the display system 200. The display system 200, in conjunction with the display driver (not shown), may be configured to display a virtual organ object (e.g., 1000) overlaid over the user's view of the real-world through the lenses 104, 106.

Various techniques for displaying virtual objects using head-mounted, or other non-wearable augmented reality devices are known and may be used with embodiments of the present invention. In one embodiment, the display system 200 may be in communication with the processor 210 and may include projectors 201 that project an image onto a surface, such as the micro display. The processor 210 may process image data, such as, for example, a three-dimensional model of a heart 800 (see FIG. 8), which image data is then fed into the projectors 201 for projecting an image onto the micro display, or other display surface. The projectors 201 may be configured to project an image onto an interior display surface of the micro display, such that the image is viewable by the user as overlaying the user's view of the real-world environment through the lenses 104, 106. The display system 200 may also include a light-projection system and may include a reflective coating, which reflects light projected onto a reflective surface directly into the user's retina.

In another embodiment, the display system 200 may be an optical see-through head-mounted display that places optical combiners directly in front of the wearer's eyes. The optical combiners are partially transmissive to permit the user to see the real-world through the combiners. The combiners are also partially reflective to permit the user to see the virtual objects bounced off of the combiners. In yet another embodiment, the display system 200 may use waveguides to display a virtual object overlaying the user's real-world field of view.

In yet another embodiment, the augmented reality display system may be formed as a smart contact wearable directly onto a wearer's eye. In yet another embodiment, the augmented reality display system may include non-wearable elements, such as non-wearable projectors using, for example, spatial computing, mirrors, light refractors, cameras, and the like to display information (e.g., digital data, virtual objects, etc.) within the real-world environment.

Other types of augmented reality display system technologies may also be used with embodiments of the present invention. In one embodiment, the augmented reality device 100 used in embodiments of the present invention is a Microsoft HoloLens™, which uses waveguides to overlay holograms on the user's real-world view. In yet other embodiments, the augmented reality device 100 used in embodiments of the present invention may include other known augmented reality devices, preferably head-mounted augmented reality devices. The components that implement the display element of virtual objects by the augmented reality device 100 may be referred to herein collectively as an "augmented reality display system."

The cardiac augmented reality module 202 may be configured to facilitate overlaying a virtual cardiac image over a view of the real-world through the lenses 104, 106, in accordance with known augmented reality techniques for overlaying images over a real-world view. In a further embodiment, the cardiac augmented reality module 202 may be responsible for performing some or all of the process steps described herein below with reference to the flow chart depicted in FIG. 7.

The cardiac augmented reality module 202 can be implemented as an executable instruction set that is resident in and executed by the augmented reality device 100. In one implementation, the cardiac augmented reality module 202 may be one or more programs that are stored on a computer or machine readable medium. In the exemplary implementation, the cardiac augmented reality module 202 is stored in the memory 212. The cardiac augmented reality module 202 may be a stand-alone software application or form a part of a software application that carries out additional tasks related to the augmented reality device 100. Also, while the cardiac augmented reality module 202 is implemented in software in accordance with an implementation of the present invention; such functionality could also be carried out via dedicated hardware or firmware, or some combination of hardware, firmware, and/or software.

The camera 204 includes a camera lens and may be configured to capture still images as well as video. In one embodiment, the augmented reality device 100 may include more than one camera 204. The camera lens may face forward (that is, away from the wearer's/user's face when the augmented reality device 100 is in use) to capture still images and video of at least a portion of a real world view as perceived by a user wearing the eyeglasses 102. The images captured by the camera 204 can be stored in the memory 212 for use in displaying the virtual organ object (e.g., 1000) overlaid over a real-world view as perceived by the user through the lenses 104, 106. In other embodiments, the augmented reality device 100 may include more than one camera 204 to, for example, capture a wide field of view of the real world.

The sensor 206 may be disposed on and/or within the head support member 110 and be configured to sense or detect aspects of the real-world environment, such as, for example, an orientation of the user's head. The augmented reality device 100 may include more than one sensor 206. In one embodiment, the sensor 206 can be, for example, an accelerometer or proximity sensor, or other sensor known in the art. The sensor 206 can, for example, detect when the user has removed the eyeglasses 102 for powering down the augmented reality device 100 or placing the augmented reality device 100 in sleep mode during non-use. In other embodiments, the augmented reality device 100 may include a plurality of sensors 206 to track, for example, wearer gaze and sense hand movements and gestures for use by the user input interface 208. Preferably, the augmented reality device 100 includes a multitude of sensors in order to sense the physical world that the user is within, as well as, to detect the user himself and, more specifically, his/her movements, gaze, head orientation, etc. Such sensors 206 may allow the augmented reality device 100 to combine real-world data with virtual image data in order to provide a more immersive and accurately augmented experience for the physician and/or to allow the virtual images to interact with aspects of the real-world.

The user input interface 208 is configured to allow the user to provide input to the augmented reality device 100, such as, for example, user selections, commands, and the like. In one embodiment, the user input interface includes a finger-operable touch pad disposed on the head support member 110 that can detect at least one of a position, pressure, and a movement of a finger via apparatuses and methods well-known in the art, such as capacitive sensing, resistance sensing, and the like. For example, the user may tap the touch pad with his or her finger to initiate or deactivate software applications responsible for generating and displaying cardiac images as augmented reality images in accordance with techniques described herein. In another embodiment, the augmented reality device 100 may include sensors 206 configured to sense the user's hand gestures as user input, in accordance with known methods and devices in the art of augmented reality devices. Other user input devices may be integrated into the augmented reality device 100, such as a microphone for voice recognition commands, a physical or virtual keyboard, movement sensors, gaze tracking cameras, pointing devices, and/or other user input methods and devices (not shown). For example, in some embodiments, the microphone may be communicatively coupled to a processor configured to analyze and recognize human utterances, which human utterances may correspond to voice commands recognizable by the processor to automatically command certain medical features (e.g., turning on and off ablation performed by an ablation treatment device).

The processor 210 can be, for example, a central processing unit (CPU), a controller, a microcontroller, or a microprocessor, including a "general purpose" microprocessor or a special purpose microprocessor. The processor 210 executes code stored in memory 212 and/or non-volatile storage in order to carry out operation of the augmented reality device 100. The processor 210 can provide the processing capability to execute an operating system, run various applications, and provide processing for one or more of the techniques, functions, and/or methods described herein. The terms "processor" and "processing circuity," as used herein, are intended broadly to encompass a single processor or multiple processors and other processing circuity providing the processing for one or more of the techniques, functions, and/or methods described herein. The augmented reality device 100 preferably includes one or more CPUs, as well as, one or more graphics processing units (GPUs) in order to process large amounts of image data.

The memory 212 associated with the augmented reality device 100 can be, for example, one or more buffer, register, flash memory, or random access memory (RAM). The memory 212 may also include non-volatile storage. The non-volatile storage can represent any suitable storage medium, such as a hard disk drive or non-volatile memory, such as flash memory, and the like.

The network interface 214 can include one or more network interface cards (NIC) that can provide the capability for the augmented reality device 100 to network with, for example, a personal area network (PAN), such as a Bluetooth® network, a local area network (LAN), such as a Wi-Fi network, or a wide area network (WAN), such as the Internet or a cellular mobile communications network, for example. The network interface 214 may facilitate communication over one or more wired and/or wireless network connections. The network interface 214 may facilitate communications between the augmented reality device 100, the medical system 10, the mapping system 500, and other devices and systems, such as a navigation system. For example, pre-operative image data, such as a computed tomography (CT) scan of a patient, may be transmitted wirelessly to the augmented reality device 100 via the network interface 214 for generating a virtual organ object based on the CT scan.

Medical System

Referring now primarily to FIG. 3, an exemplary system for treating tissue is shown. The system may be considered a medical system 10 and may be used for treating, ablating, diagnosing, and/or mapping one or more target tissue areas. The medical system 10 may generally include a treatment device 12, such as a treatment catheter, having one or more treatment or ablation electrodes 16 for the delivery of ablation or treatment energy and a console 18 that includes various system controls. The medical system 10 may be adapted for use with radiofrequency (RF) energy, phased RF energy, and/or pulsed field ablation (PFA) energy (delivered as square and/or sine waves) and may additionally be adapted for ablation or treatment using other energy modalities such as cryoablation and cryotherapy, ultrasound energy, laser energy, microwave energy, hot balloon treatment or ablation, or other modalities or combinations thereof. A description of exemplary PFA energy delivery techniques is described in U.S. Ser. No. 15/228,406, which application is incorporated herein by reference in its entirety.

The treatment device 12 may generally include a handle 22, an elongate body 24 having a distal portion 26 and a proximal portion 28, one or more treatment elements such as non-expandable electrodes 16 (for example, as may be used on a focal catheter), an expandable or non-expandable electrode array (for example, an expandable array having one or more carrier arms bearing a plurality of treatment/ablation electrodes 16, or an inflatable balloon 32 that may bear one or more treatment/ablation electrodes 16 (as shown in FIG. 3). Although the cryoballoon 32 is shown in FIG. 3 as having one treatment/ablation electrode strip 16, it will be understood that any number or configuration of electrodes may be used. Additionally, in some embodiments, the treatment device 12 may be used for cryoablation or cryotherapy only, in which case the cryoballoon 32 may not bear treatment/ablation electrodes 16. Further, the treatment device 12 may have a longitudinal axis 34 and one or more mapping electrodes 36. It should be understood that although the exemplary treatment device 12 depicted in FIG. 3 is shown as a cryoballoon catheter, other embodiments of the present disclosure may include other types of medical treatment devices. In other words, embodiments of the present disclosure are not limited to any particular treatment device, as many different types of medical treatment devices are well-known. Stated yet another way, the treatment device depicted in FIG. 3 is shown as an exemplary treatment device and is not intended to limit the scope of this disclosure.

The treatment device 12 may include one or more lumens. For example, the treatment device 12 may include one or more lumens for electrical wiring, steering elements, or the like. In addition to the treatment of tissue using RF energy, the medical system 10 may be used for cryotreatment procedures in which tissue is thermally affected by the circulation of a coolant within the treatment element. For example, the one or more treatment elements may include a cryoballoon 32 with, optionally, a plurality of treatment or ablation electrodes 16 for ablating tissue (as shown in FIG. 3), and the treatment device 12 may include one or more mapping electrodes 36. As a non-limiting example, the mapping electrodes 36 may be located on the elongate body 24 proximal the cryoballoon 32. In this case, the treatment device 12 may also include, for example, a fluid injection lumen in fluid communication with a coolant supply reservoir 38 and a coolant recovery lumen in fluid communication with a coolant recovery reservoir or scavenging system. Further, the coolant recovery lumen may be in communication with a vacuum to facilitate removal of fluid from the cryoballoon 32 (for example, expanded coolant). It will be understood, therefore, that reference herein to delivering energy to tissue also includes removing heat from tissue through a cryotreatment procedure.

The treatment device 12 may further include one or more sensors to monitor the operating parameters, including for example, pressure, temperature, flow rates, volume, or the like in the treatment device 12, in addition to monitoring, recording or otherwise conveying measurements or conditions of the ambient environment at the distal portion of the treatment device 12. In some embodiments, the medical system 10 may include other medical sensors, such as, for example, magnetic sensors, radio frequency identification devices (RFID), impedance sensors, contact force sensors, and the like. The sensor(s) may be in communication with the control unit associated with the console 18 for initiating or triggering one or more alerts or coolant delivery modifications during operation of the treatment device 12. One or more valves, controllers, or the like may be in communication with the sensor(s) to provide for the controlled dispersion or circulation of fluid through the lumens/fluid paths of the treatment device 12.

One or more pressure sensors 39 (see FIG. 4) may be coupled to a distal portion of the treatment device 12. The one or more pressure sensors 39 may be used to facilitate positioning of the treatment device 12 within the patient's body, and may further provide monitoring of the engagement between the treatment device 12 and a designated tissue region during a procedure. The one or more pressure sensors 39 may be located on the external surface of the elongate body 24. The pressure sensors 39 may be adjacent to each other to form a single pressure-sensing region or they may be located at discrete locations along the elongate body 24. The one or more pressure sensors 39 may be in communication with the control unit associated with the console 18.

Information from the one or more pressure sensors 39 may be transmitted to the console 18 and/or an augmented reality device 100, and this information may be used to create or modify a virtual representation of a virtual organ object 1000 (see FIGS. 10-12) to provide procedure guidance or feedback to the physician. In some embodiments, information from one or more of the sensors described herein throughout, which may be disposed on the treatment device 12 or be otherwise in communication with the augmented reality device 100 (e.g., sensors for temperature, pressure, impedance, force, ECG, etc.) can also be captured, analyzed and displayed via the augmented reality display 200 according to the principles described in the present disclosure. In one embodiment of the present disclosure, intraoperative pressure sensor data corresponding to the one or more pressure sensors on the treatment device 12 may be accessible by the user/physician of the augmented reality device 100 during the procedure for providing readily accessible positional data of the treatment device 12 to the physician. Such readily accessible, real-time data may assist the physician with steering the treatment device 12.

The console 18 may be in electrical and, if used for cryotreatment, fluid communication with the treatment device 12 and may include one or more fluid reservoirs (for example, coolant supply reservoirs 38), energy generators 40, switching systems 41, and computers 42 with displays 44, and may further include various other displays, screens, user input controls, keyboards, buttons, valves, conduits, connectors, power sources, processors, and computers for adjusting and monitoring system parameters. As used herein, the term "computer" may refer to any programmed or programmable data-processing unit having processing circuitry including a memory and processor, the memory in communication with the processor, the memory having one or more instructions or algorithms that, when executed by the processor, configure the processor to perform the calculations, analyses, and techniques discussed herein. For example, the data-processing unit and/or the control unit may include the augmented reality device 100, dedicated internal circuitry, user control device, or the like.

As a non-limiting example, the medical system 10 may include a GENius® Generator (Medtronic, Inc.) as an energy generator 40, but the GENius® Generator may also record data from the device, and therefore also be referred to as a "computer." Further, the energy generator 40 may include one or more displays 46, user input devices, controllers, data storage units, or the like. The computer(s) 42, energy generator 40, and/or console 18 may include one or more processing units that are in electrical communication with the one or more electrodes 16, 36 and one or more fluid valves (for example, if the system is configured for cryotreatment). As discussed above, each processing unit 48 may have processing circuitry that includes a memory and processor, with the processing circuitry being configured to receive data from the treatment device 12, process data, and to communicate data to a navigation system 50. Additionally, although the energy generator 40 and navigation system 50 are shown as being external to the console 18, all or a portion of these components may alternatively be located within the console 18, within the augmented reality device 100, and/or integrated with the computer 42 and other components of the console 18.

As a non-limiting example, the navigation system 50 may be the LOCALISA™ system (Medtronic, Inc., Minneapolis, Minn.) or a similar system. The LOCALISA™ system, for example, is a system to localize a catheter or lead in the heart and to display the location graphically on a display 52. The navigation system 50 may include an energy generator that is configured to deliver alternating current (AC) energy from three AC sources at three separate frequencies in the 30 kHz region (for example, 30.27 kHz, 30.70 kHz, and 31.15 kHz) to external electrode patches 54. In some embodiments, such a system may be adapted or reconfigured to deliver the alternating current electricity at a single frequency to the external electrode patches 54. External electrode patches 54, which may be part of the navigation system 50, are used to orient three current sources orthogonally in X, Y, and Z planes, although it will be understood that other system components may be used to generate the X-, Y-, and Z-plane current sources. In each plane, a voltage continuum is created from one electrode patch 54 in a pair to the other of the pair such that a treatment/ablation electrode 16 in that plane will act as the wiper of a potentiometer. The voltage measured by the treatment/ablation electrode(s) 16 and/or the mapping electrode(s) 36 will indicate the treatment device's position in the plane. Filters may be used to select one of the three frequencies and each plane's voltage can be obtained. Thus, the electrode's three-dimensional location can be determined. In another embodiment of the system disclosed herein, however, a single frequency may be time-division multiplexed into separate divisions for the X plane, Y plane, and Z plane, to determine the device's location.

In preferred embodiments, the display 52 of the navigation system 50, the displays 44 of the console 18, the displays 46 of the energy generator 40, and various other displays, screens, user input controls, keyboards, buttons, and the like, discussed herein above with reference to the overall medical system 10 in FIG. 3 may be omitted, replaced, or otherwise rendered unnecessary for the physician/user by the augmented reality display system 200 of the augmented reality device 100. In other words, advantageously, the multitude of conventional displays/monitors associated with existing medical systems may not be required with embodiments of the present disclosure.

Figure 4:
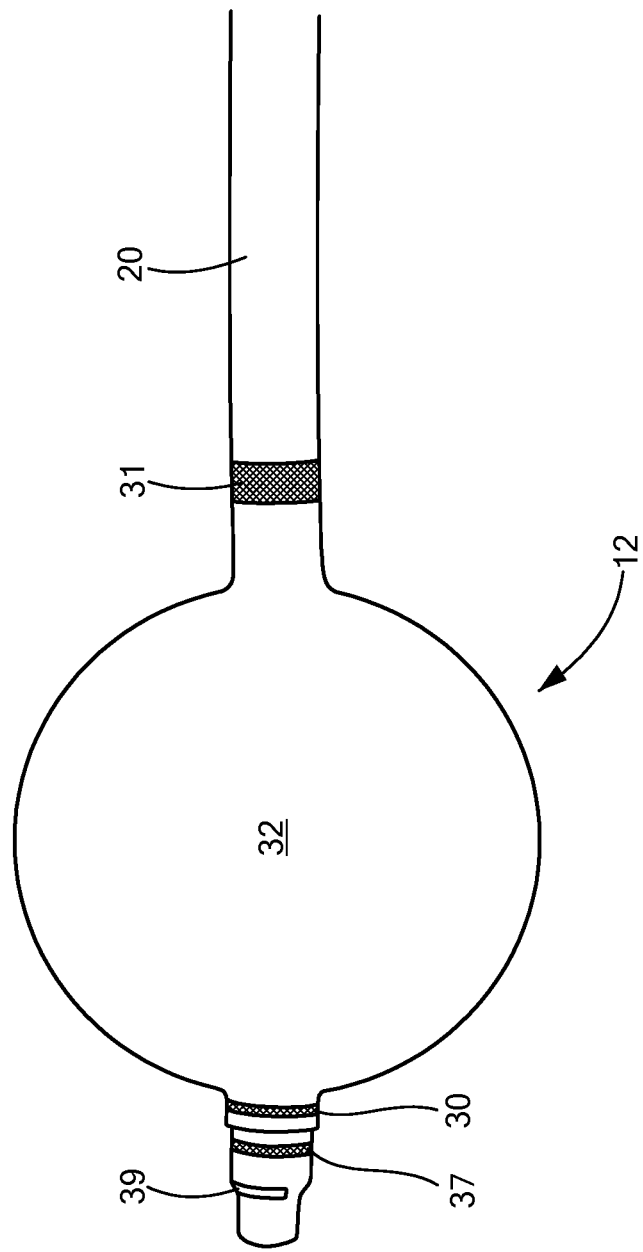
FIG. 4 illustrates an exemplary medical device within the medical system of FIG. 3 in accordance with the present disclosure.

Referring now primarily to FIG. 4, a close-up view of a distal portion of an embodiment of the treatment device 12 is shown. In one embodiment, the treatment device 12 is a cryoballoon catheter. The treatment device 12 may include the cryoballoon 32 and one or more distal electrodes 30 and one or more proximal electrodes 31. The treatment device 12 may further include a reference electrode (now shown) and one or more thermocouples 37 if the electrodes 30, 31 are not configured to measure temperature. The electrodes 30, 31 may be composed of an electrically conductive material suitable for sensing impedance and, optionally, temperature. The electrodes 30, 31 and thermocouple 37 may be coupled to, affixed to, disposed about, integrated with, or otherwise located on a distal portion of the treatment device 12.

The thermocouple 37 may be located a distance from the distal electrode 30. For example, the thermocouple 37 may be located approximately 2 mm distal to the distal electrode 30. Temperature monitoring may provide an additional and/or redundant means of assessing the quality of the freeze and propagation of the freeze in the tissue, which provides an indication of the lesion quality. As a non-limiting example, the cryoballoon 32 may have a diameter of approximately 23 mm to approximately 28 mm.

The distal electrode 30 may be located immediately adjacent to the cryoballoon 32 and the proximal electrode 31 may be located proximal to the cryoballoon 32, such as on the distal portion of the elongate body 24. For example, the distal electrode 30 may be adjacent to or may abut the distal end of the cryoballoon 32. However, the proximal electrode 31 may alternatively be located on a sheath or a separate catheter. The proximal electrode 31 may be somewhat larger than the distal electrode 30, and may serve as the indifferent in a bipolar impedance circuit or reference electrode. The larger size of the proximal electrode 31 may minimize the impedance drop on the electrode 31, making the circuit more sensitive to change on the distal electrode 30. Since the electrode 31 is proximal to the cryoballoon 32, it may be more sensitive to occlusion changes because the direct electrical path through the blood pool is eliminated. The placement of electrodes 30, 31 shown in FIG. 4 additionally may allow the treatment device 12 to be integrated with an electropotential navigation system, such as, NavX, CARTO 3, Rhythmia, and the LOCALISA™.

In addition to sensing impedance (and therefore lesion quality and PV occlusion, as discussed herein), the electrodes 30, 31 may also be configured for mapping cardiac tissue (for example, recording cardiac electrograms) from adjacent tissue. In a non-limiting embodiment, additional discrete electrodes (not shown) may be radially arranged in a distal housing coupled to a distal portion of the cryoballoon 32, with each additional discrete electrode protruding from the housing (for example, dome shaped) to facilitate local tissue depolarization for tissue mapping. Additionally or alternatively, the additional electrodes may be used for electrical impedance tomography imaging to visualize, i.e., "see" the ice formation of the cryoablation. Information from the thermocouple 37 and/or electrodes 30, 31 may be transmitted to the console 18 and/or an augmented reality device 100, and this information may be used to create or modify a virtual representation of a virtual organ object 1000 (see FIGS. 10-12) to provide device location information and/or procedure guidance or feedback to the physician.

In some embodiments, the medical system 10 may also include a video camera, which may be disposed, for example, at a portion of the treatment device 12. The video camera may be configured to wirelessly transmit video signals to the augmented reality device 100 for display via the augmented reality display system 200. The video may advantageously provide real-time visual feedback to the user of the augmented reality device 100 during, for example, a medical or surgical procedure.

Mapping System

Figure 6A:
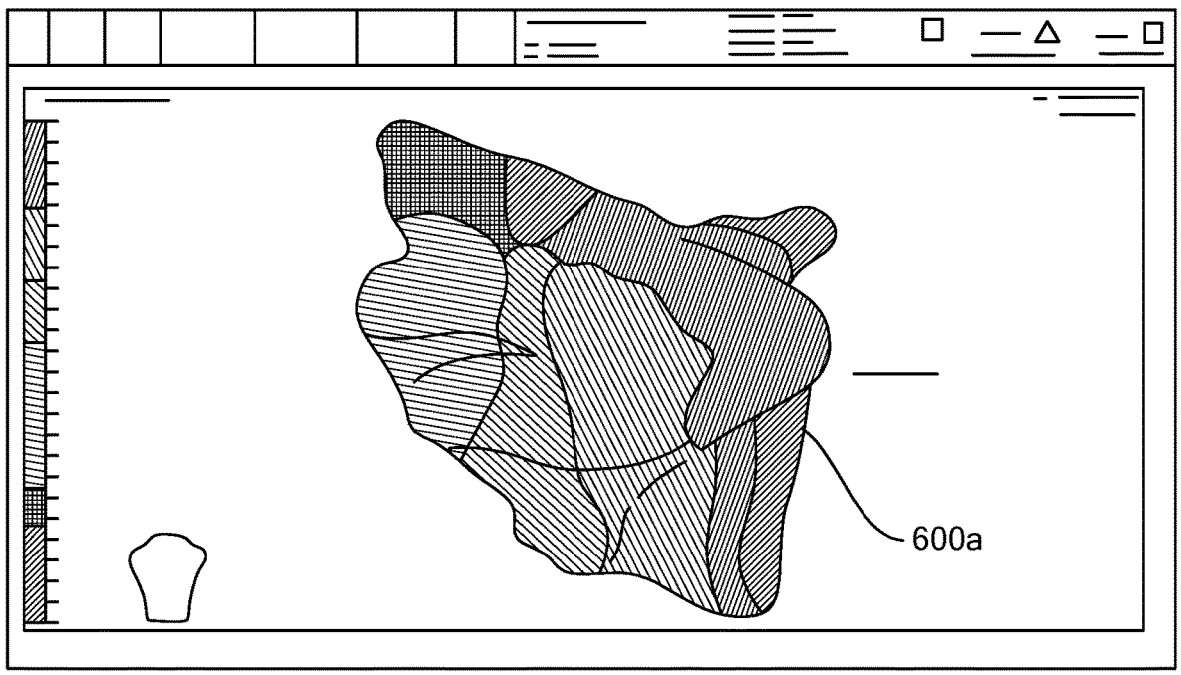
FIGS. 6*a-b* illustrate exemplary mappings of a heart of the patient from FIG. 5 in accordance with embodiments of the present disclosure.
Figure 6B:
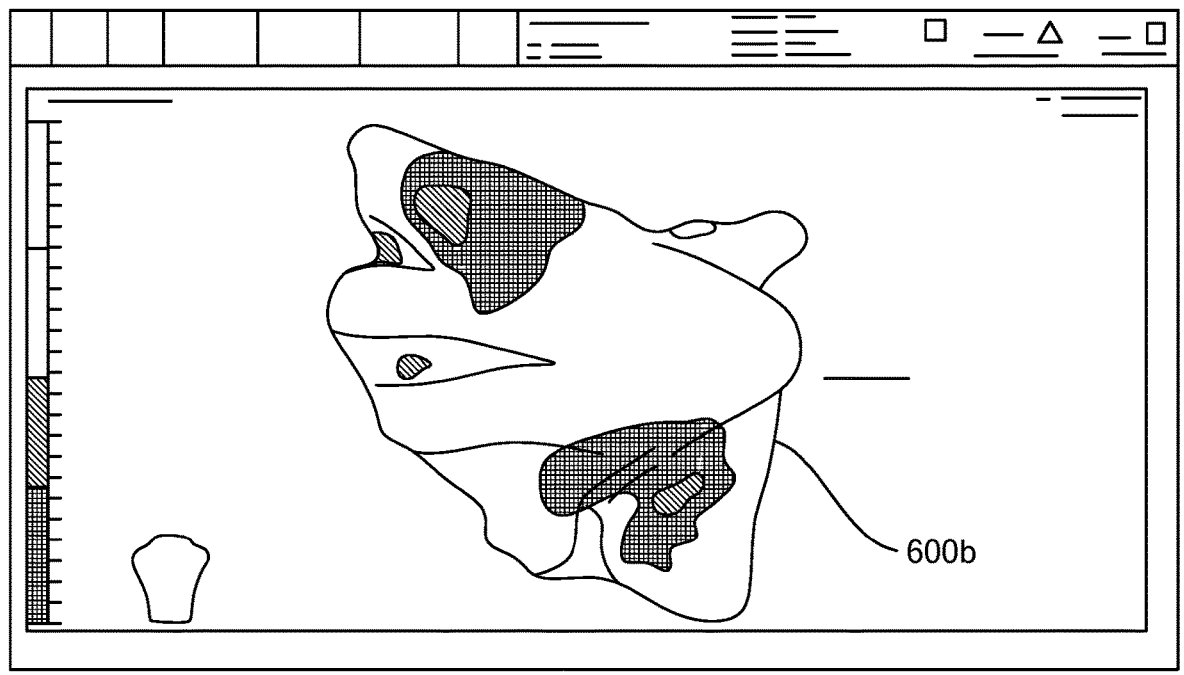

Referring now primarily to FIGS. 5 and 6a-b, an exemplary mapping system 500, in communication with the medical system 10 and/or the augmented reality device 100, will be described. As used herein, the term "mapping" is intended to indicate one or more voltage recordings, such as millivolt level voltages, known as intracardiac electrograms (EGM), by a cardiac electrophysiology mapping and/or recording system, such as the mapping system 500. In addition, the term "mapping" may also be used herein to indicate the analyses of such intracardiac EGM detection of the depolarization wave front moving through the cardiac muscle. As described herein below, the mapping system 500 may also display such wave fronts moving over a three-dimensional (3D) rendering of a cardiac surface.

The exemplary mapping system 500 may include an array of electrodes 502 disposed on a support surface 508 that may be applied to a body surface of a patient 506, such as, for example, a support surface (e.g., vest) that can engage the body surface of the patient, specifically, the chest area. The ECG information from these electrodes can be overlaid on the surface of the virtual heart model to provide the physician with information about the electrical activity of the heart. This information can be presented prior, during and after ablation to demonstrate therapy efficacy based on the change in electrical patterns of the heart. In other embodiment, the array of electrodes 502 may be directly attached to the patient's skin. In yet other embodiments, the support surface 508 may be formed as other types of non-wearable support surfaces, but should be electrically conductive. In one embodiment, electrical signals may be provided through the electrodes 502 to monitor and record the electrical activity of the patient's heart 800. Thus, non-invasive electrophysiological mapping can be performed on the patient's heart 800. In a further embodiment, the electrical activity may be recorded and analyzed by a processing system 504, such as a control and analyses system, that may collect, store in memory, analyze the data, and render EGM data on a display, such as, for example, the augmented reality display system 200. Other known types of mapping systems may be used with embodiments of the present disclosure.

In one embodiment, the mapping system 500 may further include other sensors disposed on the support surface 508, such as, for example, an accelerometer or other position or movement sensors to detect position and movement, and assist with registration of the patient's heart location, breathing, body position, and the like, which may change during the medical procedure.

It should be understood that although the term "patient's heart" is used herein throughout, other embodiments of the present disclosure described herein may include methods and apparatuses associated with a different organ, or an anatomical feature (instead of or in addition to the heart). For example, in some embodiments, data from accelerometers, PN stimulation, esophageal temperature probes, etc. may also be displayed via the augmented reality system of embodiments of the present disclosure, for example, for safety purposes or otherwise monitoring the patient. In addition, embodiments of the present disclosure may include methods and apparatuses associated with a subject that may not be considered a patient, such as, for example, a cadaver or an animal, as the case may be in embodiments for, for example, research or teaching purposes. Accordingly, as used herein, the term "subject" is intended broadly to include patients as well as non-patient subjects.

Figure 7:
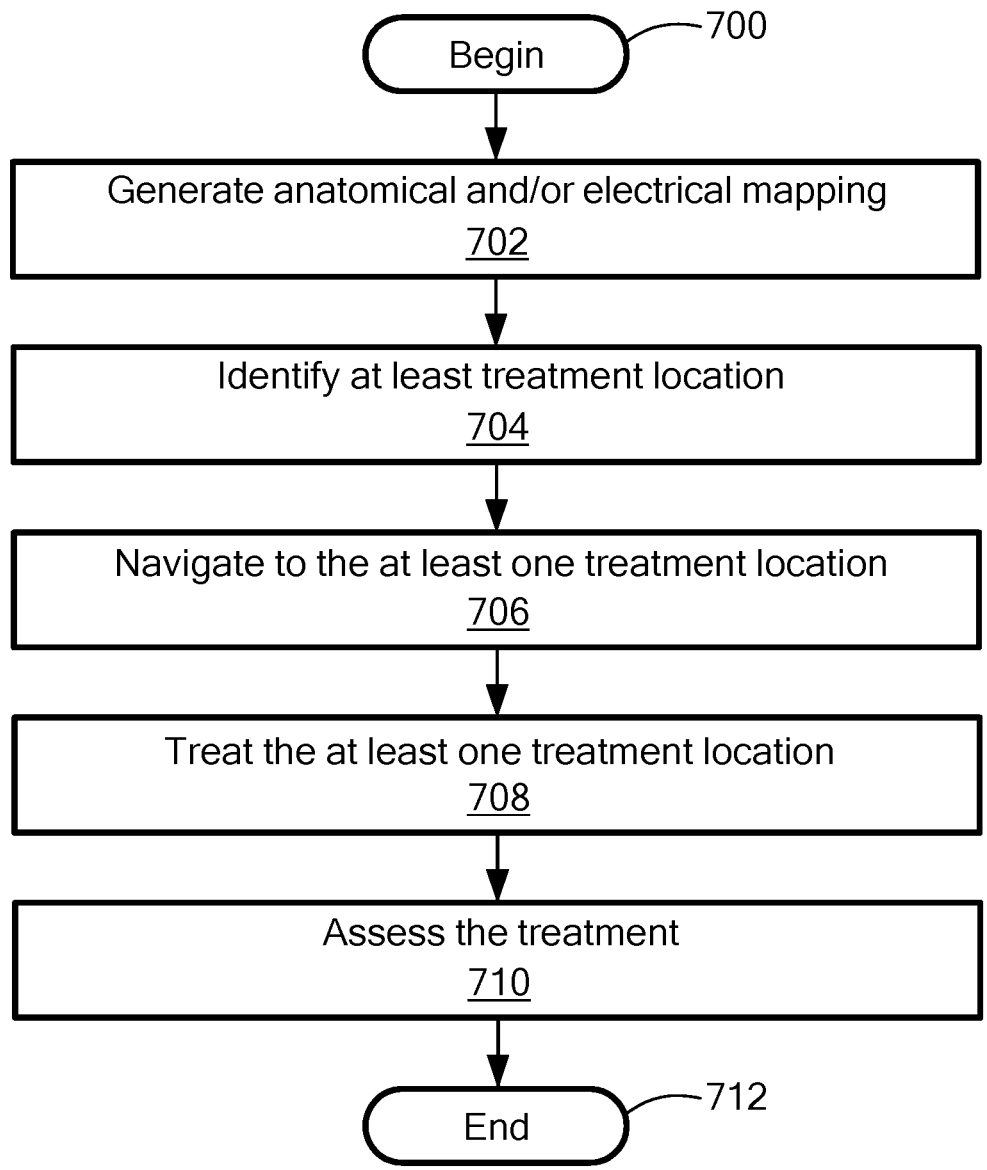
FIG. 7 illustrates an exemplary method in accordance with embodiments of the present disclosure.

Method for Providing an Augmented Reality Solution to Enhance Cardiovascular Procedural and/or Surgical Mapping, Navigation, and Diagnostics Referring now to the flow chart shown in FIG. 7, with reference also to FIGS. 1-6 and 8-12, an exemplary method of using the augmented reality device 100 of FIGS. 1-2, the medical system 10 and navigation system 50 of FIGS. 3-4, and the mapping system 500 of FIG. 4, in accordance with principles of the present disclosure is described.

It should be understood that although the terms "navigation system" and "mapping system" are referred to herein separately, some embodiments of the present disclosure may be considered a single system with a plurality of components or sub-systems that provide navigation and mapping functionality, as described herein. Accordingly, as used herein, the term "navigation system" is intended broadly cover a navigation system separate from a mapping system, as well as, a component or sub-system within an overall system that performs the navigation techniques and functions described herein (e.g., the navigation techniques described with reference to the exemplary navigation system 50). Likewise, the term "mapping system" is intended broadly to cover a mapping system separate from a navigation system, as well as, a component or sub-system within an overall system that performs the mapping techniques and functions described herein (e.g., the mapping techniques described with reference to the exemplary mapping system 300).

In addition, for clarity of description, the exemplary method depicted in the flow chart of FIG. 7 will be described in the context of a cardiac ablation procedure for the treatment of atrial fibrillation; however, it should be understood that other embodiments of the present disclosure may be used to enhance other types of medical procedures, including without limitation installation of a heart monitor/pacer, a mitral valve replacement, a stent, a left atrial appendage closure device, and other cardiac devices used in both invasive and minimally invasive procedures.

Although FIG. 7 shows a specific order of executing functional logic blocks, the order of executing the blocks may be changed relative to the order shown. Also, two or more blocks shown in succession may be executed concurrently or with partial concurrence. Certain blocks may also be omitted for the sake of brevity. And some blocks are merely exemplary steps in an exemplary implementation, but are not required in order to be in accordance with the present invention.

The method may begin at step 700 and immediately proceed to step 702, where an anatomical and/or electrical mapping is generated to assist a physician 1002 (see FIG. 10) with pre-operative planning, as well as, for intraoperative guidance (e.g., visualization during a surgical procedure and treatment assessment).

In one embodiment, the processing system 504 of the mapping system 500 may receive and analyze the electrogram data and may render the electrical mapping corresponding to the EGM. As used herein, the term "electrogram data" is intended broadly to encompass data from an electrogram as well as data obtained from an analysis of the electrogram or otherwise derived from the electrogram. In another embodiment, the processing system 504 (or another computing device in communication therewith, such as, for example, 100 or 300) may create a 3D model of the patient's heart 800 and render the EGM data as moving over a cardiac surface of the 3D model of the heart 800, as shown, for example, in FIGS. 6a-b. FIGS. 6a and 6b each illustrate an exemplary rendering 600a, 600b of the EGM data moving over portions of the cardiac surface of the patient's heart 800.

In one embodiment, the 3D rendering 600a or 600b may be based on pre-operative image data of the patient's heart 800, such as, for example, image data associated with a magnetic resonance imaging (MRI), an x-ray, an ultrasound, a fluoroscopy, an electrocardiogram, and/or a computed tomography (CT) scan of the patient's heart 800. Of note, such image data is typically obtained prior to a surgical procedure in order to determine if the surgical procedure is warranted. Techniques and devices for providing pre-operative image data are well-known in the art and therefore will not be described in great detail herein.

In one embodiment, the augmented reality device 100, or more specifically the one or more processors 210, may create the 3D model based on received pre-operative image data. In another embodiment, a separate computing device may create the 3D model and may communicate or otherwise provide the 3D model to the augmented reality device 100. In one embodiment, the 3D model may be created by, for example, a software application that may apply various 3D modeling techniques on the pre-operative image data. The 3D modeling techniques may include, for example, segmenting the pre-operative image data to identify the area(s) of interest, followed by mesh refinement of the area(s) of interest, and further 3D refining techniques, such as repairing the mesh, correcting errors, smoothing surfaces, and the like. Applications and techniques for transforming medical imaging data into 3D models are known in the medical industry to, for example, 3D print replacement or model anatomical parts. These and other known applications and techniques for creating 3D models may be used in embodiments of the present invention to create a 3D model for use by the augmented reality device 100.

Alternatively, the 3D rendering 600a or 600b may be based on a 3D model of a generic heart, to reduce the high costs associated with existing imaging techniques. In one embodiment of the present disclosure, the 3D model of the patient's heart 800 may be rendered as a 3D virtual organ object 1000 (see FIG. 10) and may include associated vasculature. The 3D virtual organ object 1000 may be augmented and displayable via the augmented reality display system 200 of the augmented reality device 100, rather than a conventional monitor. In yet a further embodiment, the 3D virtual organ object 1000 may be further augmented with the EGM data (e.g., see FIGS. 6a-6b), showing the electrical characteristics, such as, the depolarization wave fronts moving over the surface of the 3D virtual organ object 1000.

In a preferred embodiment, the 3D model may be a 3D model of the patient's heart 800 and should include a 3D model of the area(s) of interest, such as, at least one target treatment anatomy of the patient. The particular areas of interest may be the areas of the heart 800 relevant to the surgical procedure to be performed on the patient's heart 800. The target treatment anatomy may be considered one or more anatomical features of the patient that are intended for treatment, such as, for example, an occlusion of the right inferior pulmonary vein 804, the right superior pulmonary vein 806, the left inferior pulmonary vein 808, and/or the left superior pulmonary vein 810 (see FIG. 8). In one embodiment, the 3D model may be a 3D model of the patient's vasculature, or may include at least a portion of the patient's vasculature.

Figure 8:
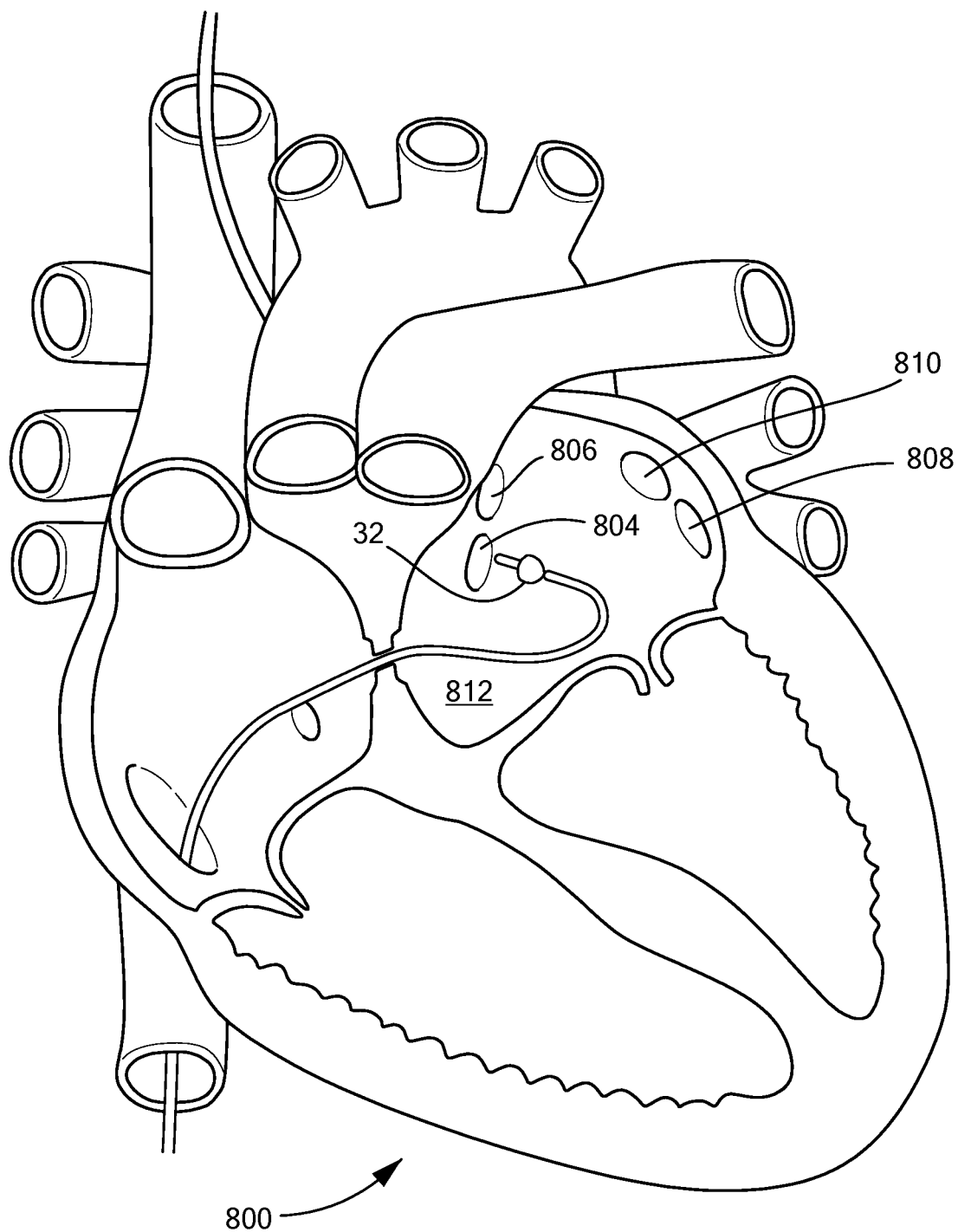
FIG. 8 illustrates a cross-sectional view of the heart of the patient from FIG. 5 in accordance with an embodiment of the present disclosure.

In one embodiment, the 3D model includes a cross-sectional view of the heart 800 that shows the area(s) of interest, such as the cross-sectional view depicted in FIG. 8. Alternatively, the 3D model may be a surface model of the surface of the patient's heart 800, such the 3D renderings 600a, 600b depicted in FIGS. 6a and 6b. In one embodiment, a user may input (into the augmented reality device 100 or another computing system in communication with the augmented reality device 100) a selected view (cross-sectional or surface) and/or surgical procedure prior to the creation of the 3D model. Accordingly, the 3D model may be created to include the selected view or multiple views that may be relevant for the selected surgical procedure. In another embodiment for systems dedicated to a particular type of surgical procedure, the selected view(s) may be a default view. In further embodiments, the 3D model may include a plurality of cross-sectional views of the heart 800 from which the surgeon/physician 1002 may select to view via the augmented reality device 100 on-the-fly during pre-operation planning as well as during the procedure itself.

In some embodiments, a neural network algorithm using artificial intelligence can be configured to accept a plurality of different formats of scans such as MRI, CT, ultrasound, echo, etc. and may automatically segment and reconstruct the anatomy depicted in such scans to render the virtual object in 3D as, for example, a single 3D image of the anatomy, using the data from each of the plurality of different formats. The 3D reconstruction may be automatically deployed and registered to the patient in the mixed reality space. The system may in some embodiments be configured to use automatic vision recognition techniques to determine blood volumes and identify rigid structures to define anatomical boundaries and landmarks for the 3D image.

Identify at Least One Treatment Location

Figure 10:
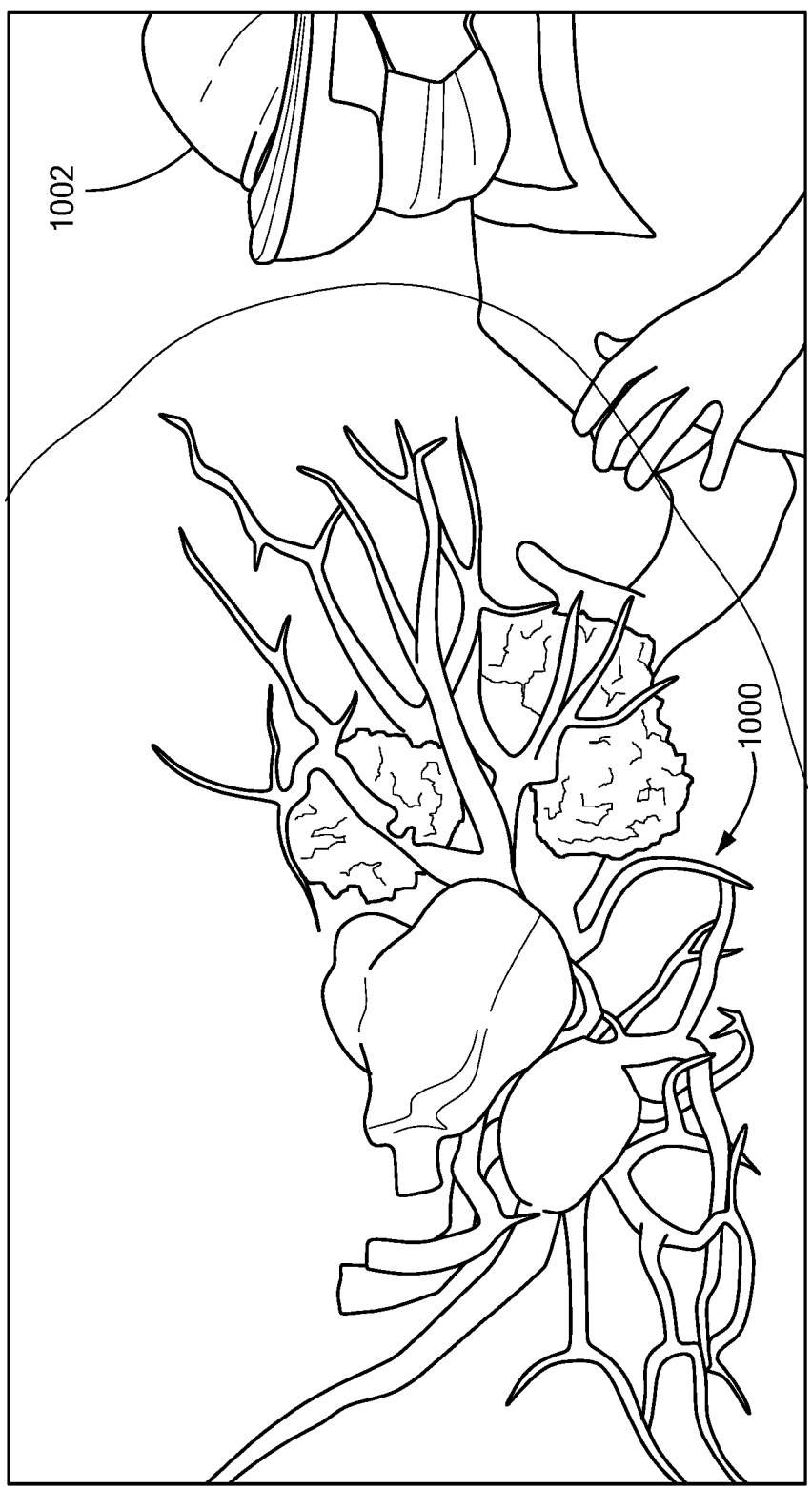
FIG. 10 illustrates a virtual organ object being rendered by the augmented reality device of FIG. 1 in accordance with one embodiment of the present disclosure.
Figure 11:
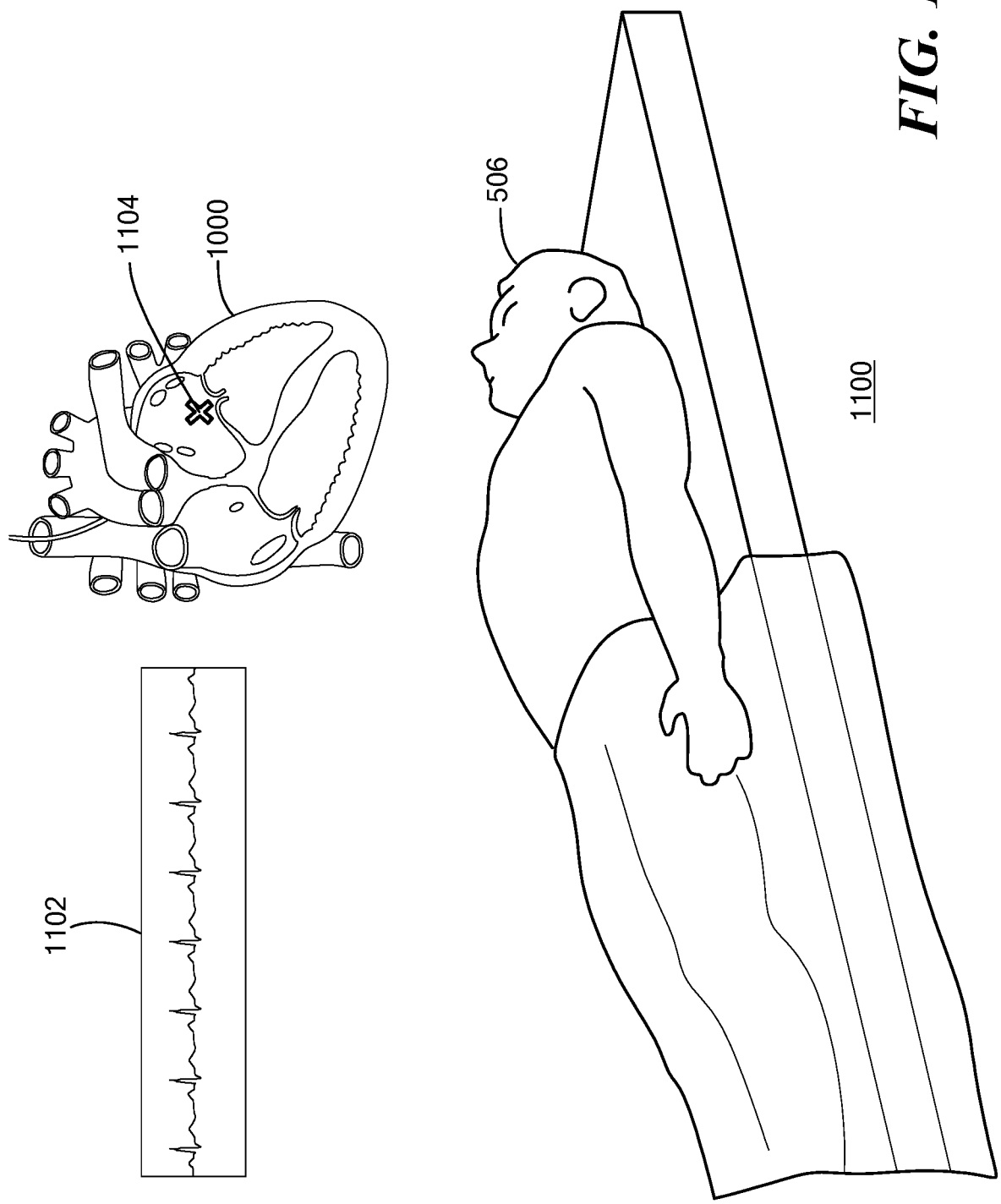
FIG. 11 illustrates a physician's augmented reality view, via the augmented reality device of FIG. 1 (not shown), in a surgical room viewing a real-world patient on an operating table simultaneously with a free-floating virtual organ object in accordance with an embodiment of the present disclosure.

In step 704, at least one treatment location is identified. Having rendered the 3D virtual organ object 1000 and/or electrogram data, preferably on the 3D virtual organ object via the augmented reality display system 200 (as discussed above), at least one treatment location may be identified on the virtual organ object 1000. In one embodiment, the treatment location may be one or more of the pulmonary veins 804, 806, 808, 810 (see FIG. 8), which may be intended for treatment by, for example, ablation. Other treatment locations may be identified in other embodiments, depending on the procedure, such as, for example, a lead placement location, a left atrial appendage, and a mitral valve. By being able to visualize the patient's heart 800 in a 3D environment including associated data, such as, for example, electrical activity of the patient's heart 800, the physician 1002 can better identify treatment locations for the procedure. Such identification may be performed during the pre-operative planning stage and/or may also be performed during the procedure. In embodiments, rendering the virtual organ object 1000 and/or the electrogram data during the procedure may provide the physician 1002 with a 3D visual reference within his/her field of view via the augmented reality display system 200 as an immediately accessible visual guide. Advantageously, in such embodiments, the physician 1002 may not be required to rely on existing conventional monitors that require the physician 1002 to constantly look away from the patient 506 in the surgical room 1100 (as illustrated in FIGS. 10 through 12).

The virtual organ object 1000 may be displayed by the augmented reality device 100, overlaying a real-world environment, such as the surgical room 1100, as seen by the user 1002 through the lenses 104, 106 of the augmented reality device 100. Stated another way, the real-world environment 1100 may be considered simultaneously viewable by the user 1002 of the augmented reality device 100 through the augmented reality display system 200. For example, FIGS. 10-11 show the virtual organ object 1000 floating in free-space, and FIG. 12 shows the virtual organ object 1000 being attached to and overlaying the patient's heart 800.

Figure 12:
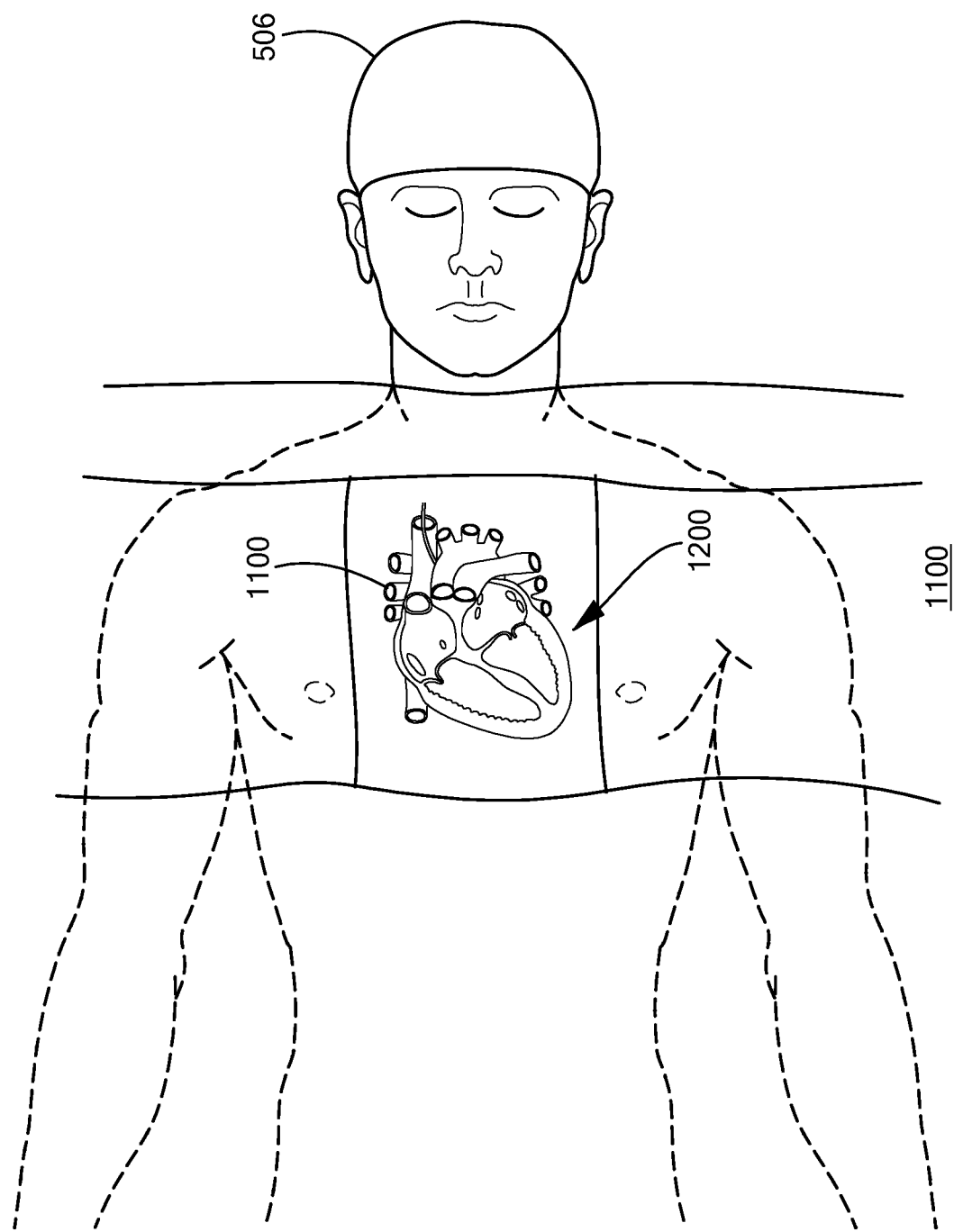
FIG. 12 illustrates the physician's augmented reality view peering down on the real-world patient of FIG. 11, with the virtual organ object attached to the real-world patient's heart during the surgical procedure in accordance with an embodiment of the present disclosure.

In some embodiments, the virtual organ object 1000 may cover a portion of the user's real-world field of view (see FIG. 12 for example where the patient's chest is covered by the virtual organ object 1000). In other embodiments, the virtual organ object 1000 may be semi-transparent such that the portion of the user's real-world view that would be covered is still viewable by the user 1002 beneath the virtual organ object 1000. As used herein, the term "overlay" is intended broadly to encompass both such embodiments where parts of the real-world are covered and where such parts are still viewable by the user beneath a semi-transparent virtual object.

In addition, the term "real-world environment" and "real-world object" are intended to indicate the physical world; in other words, the physical environment and physical objects therein. An example of a real-world environment is the surgical room 1100. Of course, as the user 1002 moves around the real-world environment viewable through the lenses 104, 106 changes. In other words, real-world objects may move in and out of the user's 1002 field of view as the user 1002 move about.

Accordingly, the virtual organ object 1000 may be configured to move with the movement of the user 1002 so that the virtual organ object 1000 is continuously within the user's 1002 field of view as the user 1002 moves about his/her environment. Alternatively, in some embodiments, the augmented reality device 100 may be configured to attach (also referred to in the AR field as "register") the virtual organ object 1000 to a physical object, such as the patient's anatomy (e.g., heart or chest), as seen in FIG. 12. When the virtual organ object 1000 is attached/registered to the patient's anatomy 1200, a movement of the user 1002 away from the patient's anatomy 1200 (e.g., the physician 1002 leaves the surgical room 1100) results in the virtual organ object 1000 moving out of the user's 1002 field of view. In other words, to provide a look-and-feel of virtual objects interacting with real-world objects, the augmented reality device 100 may be configured to attach the virtual objects to real-world objects. This may enhance the physician's 1002 immersive experience with the virtual organ object 1000.

In some embodiments, the augmented reality device 100 may be configured to allow the user 1002 to provide a user input selecting between an attachment mode and a non-attachment mode. In further embodiments, the augmented reality device 100 may configured to allow the user 1002 to provide a user input selecting a real-world object to attach the virtual organ object 1000. In yet other embodiments, the augmented reality device 100 may be configured to provide these features as default non-selectable features.

As used herein, the terms "surgeon" and "physician" are used interchangeably and are intended to indicate a medical practitioner. In some embodiments, one or more of the medical practitioners observing or participating in a medical procedure in accordance with embodiments of the present disclosure may be avatars of real-world medical practitioners viewable via the augmented reality display system 200. Further, the terms "surgical room" and "medical procedure room" may be used interchangeably and are intended to indicate an area or a room within which the medical/surgical procedure (e.g., PV occlusion, ablation, LAA closure, etc.) are or will be performed, as the case may be.

A variety of known techniques for registering a virtual object may be used with embodiments of the present invention. For example, in one embodiment, outward-facing video cameras 204 disposed on, or embedded within the augmented reality device 100 may capture video of the user's view of the real-world environment. The video data may be analyzed by the processors 210 to identify real-world objects in the user's field of view. Accordingly, the virtual organ object 1000 may be rendered based on a location of the identified real-world objects (e.g., patient anatomy 1200). Movement of the real-world object may also be tracked by the cameras 204 and the processors 210 such that the movements of the virtual organ object 1000 can be mapped to the movement of the real-world object. Embodiments of the present disclosure may use existing augmented reality devices, such as, for example, Microsoft's HoloLens™. Aspects of the present disclosure may include software code (or other computer-executable instructions, e.g., the cardiac augmented reality module 202) configured to use the augmented reality device 100 to identify a real-world patient, overlay the virtual organ object 1000 created based on the patient's pre-operative image data, and/or register the virtual organ object 1000 to the patient's anatomy 1200.

In addition, sensor data from sensors in the medical system 10, the navigation system 50, and/or the mapping system 500 may be displayable by the augmented reality device 100 within the physician's 1002 field of view, overlaying the real-world environment. Data, such as temperature readings, pressure, electrical properties, and the like, may be displayed by the augmented reality device 100 via the augmented reality display system 200 in real-time during the procedure in order to assist the physician with being provided a real-time assessment of the efficacy of the procedure so that the physician can adjust his/her approach on-the-fly, as warranted.

In one embodiment, the sensor may be considered an intracardial sensor (i.e., within the patient's heart), such as, for example, the treatment/ablation electrode 16. In a further embodiment, the sensor may be configured to sense an electrical parameter of the heart 800, such as, for example, an impedance measurement or a voltage measurement associated with the patient's heart beat (e.g., electrogram). The sensor data may be displayed via the augmented reality display system 200 in real-time for the physician 1002. For example, electrical mapping data 1102 may be displayed and overlaid over the real world environment 1100 during the surgical procedure, as shown in FIGS. 11 and/or FIGS. 6a-b. This may provide the physician 1002 with real-time data on the electrical activity of the patient's heart 800, within the physician's 1002 operating field of view.

In other embodiments, the medical sensor(s) may include a temperature sensor (e.g., thermocouple 37) or the one or more pressure sensors 39. Such sensor data may allow the physician 1002 to make an informed assessment as to the location of a treatment device, such as for example, the treatment device 12, and/or the quality of a treatment. For example, cryoablation requires extremely low temperatures in order to freeze the tissue. Temperature data from the thermocouple 37 indicating a temperature value beneath an expected predetermined temperature value for the cryoablation may alert the physician 1002 that a lesion may not be well-formed, or that the treatment device 12 may not be properly positioned to fully occlude the PV, as will be explained in more detail herein below. In embodiments where an indication of the sensor data is displayed via the display system 200 (which may also be referred to as an augmented reality display system 200), the physician 1002 may not be required to look away from the patient in order to be alerted. In another embodiment, the sensor may be an external sensor to the patient, such as, for example, the electrode patches 54.

Navigate to and Treat the at Least One Treatment Location

Figure 9A:
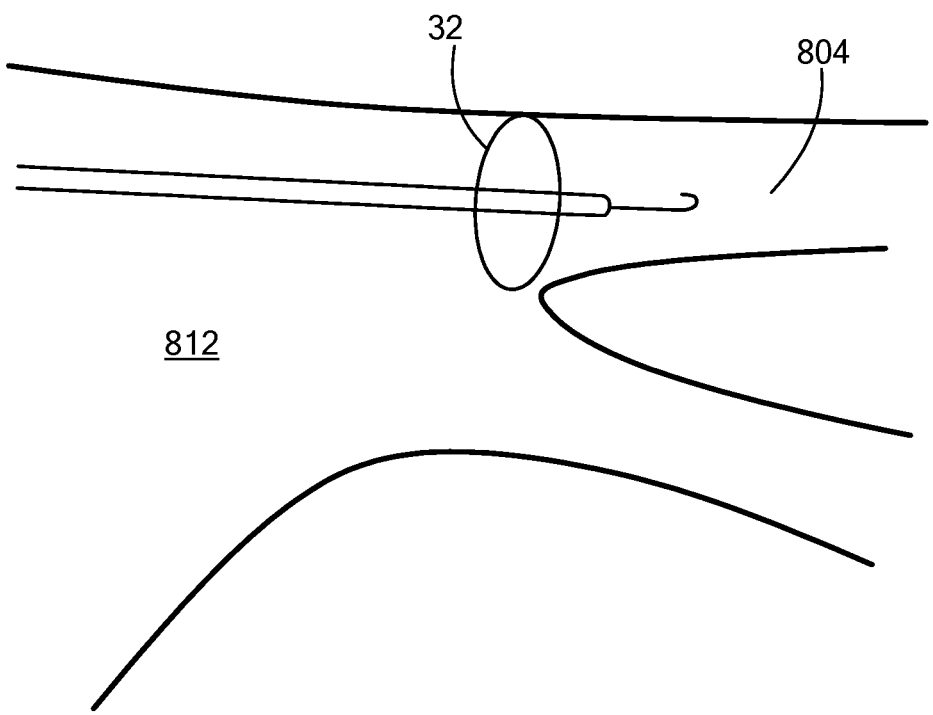
FIGS. 9*a* and 9*b* illustrate a partial occlusion of a pulmonary vein and a full occlusion, respectively, in accordance with embodiments of the present disclosure.
Figure 9B:
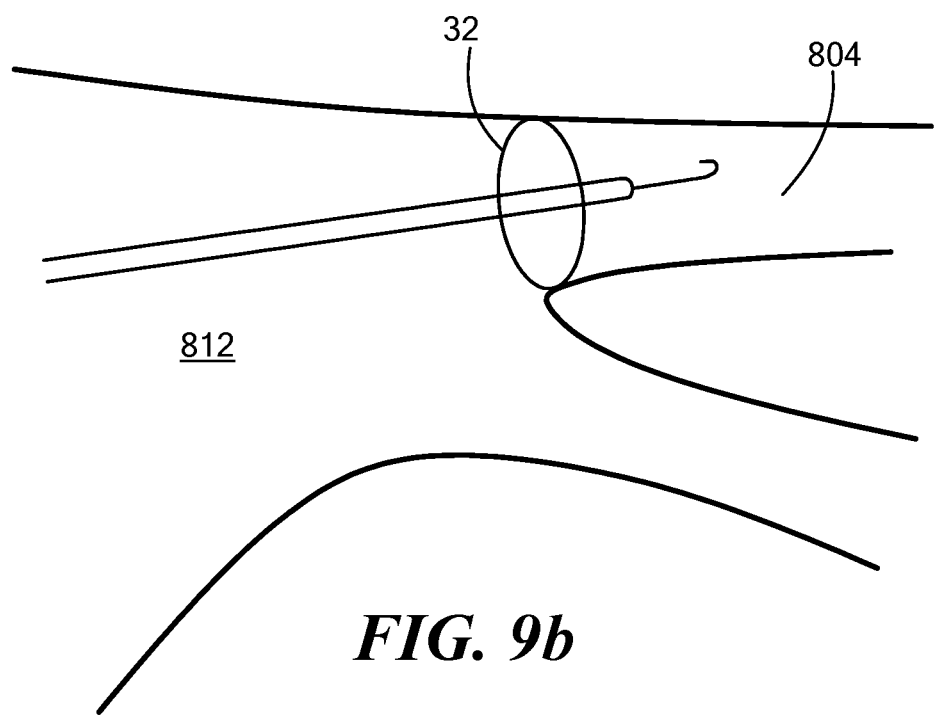

In step 706, the treatment device 12 is navigated to the treatment location (e.g., PV 804, 806, 808, and/or 810) during the surgical procedure before the delivery or initiation of treatment. In an exemplary embodiment, the treatment element, such as the cryoballoon 32, is navigated towards the right inferior pulmonary vein 804, as shown in FIG. 8 and FIGS. 9a-b, for a pulmonary vein ablation procedure (which may also be referred to as a pulmonary vein isolation (PVI) procedure). It should be understood that the cryoballon 32 shown in FIGS. 9a-b is merely exemplary and that other shapes and configuration of a cryoballoon may be used with embodiments of the present invention, such as, for example, an adjustable diameter cryoballoon, or a non-spherical cryoballoon. Also, as used herein, the term "PV tissue" or "pulmonary vein tissue" may include tissue of the PV ostium, the PV antrum, LA wall tissue, and/or tissue at the junction between the LA and PV, and is not limited to tissue within the PV. In fact, ablation of tissue within the PV may be undesirable. The inflated cryoballoon 32 may be navigated to the pulmonary vein (PV) ostium to occlude the PV, or block the flow of blood from the PV into the left atrium (LA) 812 of the heart. Occlusion of the PV not only serves to position the cryoballoon 32 to create a circumferential lesion around the PV ostium, but also prevents warm blood from flowing over the portions of the cryoballoon 32 that are in contact with the target tissue, thereby enhancing the ability of the cryoballoon 32 to reach sufficiently cold temperatures for creating permanent, and circumferential, cryoablation lesions on or in the target tissue. If the PV is not completely occluded (see FIG. 9a), blood flow past the cryoballoon 32 may have the effect of raising the temperature of the cryoballoon 32, possibly resulting in the formation of reversible lesions on or in the target tissue. The blocked blood within the PV may be referred to as "stagnant" blood, whereas the blood within the LA may be referred to as "flowing" blood, as blood may still enter the LA from the other three PVs that are not being occluded by the treatment device 12. The medical system 10 allows the physician 1002 to evaluate occlusion in real time and without the use of fluoroscopic contrast dye.

In step 708, the treatment location, such as the PV 804, may be treated by, for example, ablation of the PV tissue. Continuous impedance and temperature measurements may be taken by the electrodes 30 and/or 31 during device placement and, subsequently, treatment by cryoablation. Impedance may increase as at least part of the cryoballoon 32 is inserted into the PV, which may indicate either full occlusion (see FIG. 9b) or partial occlusion (see FIG. 9a). The amplitude of the impedance increase may be used to determine whether the occlusion is full or partial and, therefore, may be used to determine whether permanent lesions are being formed. For example, a greater amplitude may indicate full occlusion, whereas a lesser amplitude may indicate partial occlusion. Full occlusion may be indicative of permanent lesion formation as a result of the ablation procedure. In some embodiments, haptic feedback may be provided by, for example, the augmented reality device, or medical tools, to provide tactile feedback to the physician indicating various medical aspects, such as, for example, indicating full occlusion or other useful information. Haptic feedback may provide an alternative to visual feedback for certain aspects of the medical procedure.

Assess Treatment

In step 710, an assessment of the treatment may be performed during and/or after the treatment based on the measurements recorded by the electrodes 31 and/or 31, thermocouples 37, pressure sensors 39, and/or other sensors. For example, if impedance and/or temperature measurements indicate that the PV is not permanently ablated and/or less than fully occluded, the treatment device 12 may be repositioned until complete PV occlusion is indicated by evaluation of the impedance and/or temperature measurements. For example, the one or more processors (such as the processor 210 of the augmented reality device 100) may be programmed to receive and process the sensor data from the one or more electrodes and/or thermocouples, and to generate an alert or visual indication to the user indicating that the treatment device 12 should be repositioned to achieve complete PV occlusion or that the treatment device 12 is already optimally positioned. Advantageously, such indications and/or alerts may be displayed via the augmented reality display system 200 or otherwise output by the augmented reality device 100. This may provide the physician 1002 with real-time feedback on the navigation of the treatment device 12 within the patient 506 during the procedure and within the physician's 1002 operating field of view. Accordingly, the physician may not be required to look away from the patient 506 during the procedure in order to view the navigation and other procedural diagnostic data.

In one embodiment, the navigation system 50 (e.g., LOCALISA™ system) is configured to continuously monitor the location/position of the treatment device 12 within the patient's heart 800 during the procedure. The processor(s) 210 of the augmented reality device 100 may be configured to continuously receive the monitored position from the navigation system 50. In a further embodiment, the processor(s) 210 of the augmented reality device 100 may be further configured to display a visual indication 1104 of the monitored position of the treatment device 12 on the virtual organ object 1000, as shown, for example, in FIG. 11. The visual indication 1104 may be any form of visual computer-displayable graphical indication, such as, for example, a blinking "X," an arrow, a circle, or other shape, and the like. The visual indication 1104 of the monitored position of the treatment device 12 is preferably continuously updated in real-time during the procedure so as to provide a real-time navigation tool for the physician 1002. As used herein, the term "continuously" and "continuous" is intended broadly to encompass periodic updates at intervals of time that are close enough to appear at least substantially continuous from a human perspective. As is known in the computing arts, any data being transferred between computing devices must occur at certain intervals of time (however short) corresponding to an internal clock speed of a processor.

In some embodiments of the present disclosure, the display of information from, for example, a cryoconsole (e.g., the console 18) may be either replicated, or exclusively presented in the augmented reality space by, for example, the augmented reality device 100 via the display system 200. In further embodiments, temperature, pressure, ECG, impedance, radio signals or any other information being communicated from the therapy device (e.g., treatment device 12) to the cryoconsole may be communicated in the augmented reality environment via, for example, the augmented reality device 100. Such information may be collected or received and recorded or stored from the cryo-console, navigation systems, EP recording system, electrical mapping system, or other ancillary subsystems and may be gathered and automatically analyzed using known transfer functions or may be fed into a self-learning computer system configured to derive its own conclusions on trends, patterns, and relationships between the data collected over time and, in some embodiments, from a multitude of procedures. In preferred embodiments, procedural data from a plurality of systems and subsystems, including those discussed herein, may be used by the self-learning computer system to inform and display useful information within the mixed reality environment (via, for example, the augmented reality device 100). In some embodiments, such information from the plurality of systems and subsystems may be automatically uploaded to a cloud based server where the information can be processed and analyzed automatically using one or more artificial intelligence (AI) algorithms. In some embodiments, the AI algorithms may be used by a processing device, such as, for example, the self-learning computer system, in communication with the cloud based server, to aggregate and analyze the information from multiple procedures at one or more remote locations to identify trends, patterns, relationships, etc. and formulate suggestions or conclusions displayable via the augmented reality display system 200 for use by the user.

The process may end at step 712.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

In the above description, it should be understood that the terminology used herein is for the purpose of describing particular embodiments only and is not intended to be limiting. The terms "a" or "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The term "coupled," as used herein, is defined as connected, although not necessarily directly, and not necessarily mechanically. The term "providing" is defined herein in its broadest sense, e.g., bringing/coming into physical existence, making available, and/or supplying to someone or something, in whole or in multiple parts at once or over a period of time. Further, unless otherwise indicated, terms such as "first", "second", "third" and so on are only used for descriptive purposes, and should not be construed as indicating or implying relative importance.

In the description of the embodiments of the present invention, it should be noted that, unless otherwise clearly defined and limited, terms such as "installed", "coupled", "connected" should be broadly interpreted, for example, it may be fixedly connected, or may be detachably connected, or integrally connected; it may be mechanically connected, or may be electrically connected; it may be directly connected, or may be indirectly connected via an intermediate medium. As used herein, the terms "about" or "approximately" apply to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. The terms "program," "software application," and the like as used herein, are defined as a sequence of instructions designed for execution on a computer system. A "program," "computer program," or "software application" may include a subroutine, a function, a procedure, an object method, an object implementation, an executable application, an applet, a servlet, a source code, an object code, a shared library/dynamic load library and/or other sequence of instructions designed for execution on a computer system. Those skilled in the art can understand the specific meanings of the above-mentioned terms in the embodiments of the present invention according to the specific circumstances.

What is claimed is:

1. An augmented reality system, the system comprising:
an augmented reality display system; and
processing circuitry in communication with the augmented reality display system, the processing circuitry configured to:
receive, from a mapping system, electrogram data associated with a subject's anatomical feature;
receive, from a navigation system, an indication of a position of a treatment device within the subject's anatomical feature;
display, via the augmented reality display system, a virtual organ object, the electrogram data associated with the subject's anatomical feature, and the indication of the position of the treatment device within the subject's anatomical feature overlaying a real-world environment viewable by a user of the augmented reality display system;
receive, from at least one sensor, an indication of an occlusion of a pulmonary vein, the indication of the occlusion of the pulmonary vein is based on a temperature measurement from the at least one sensor; and
display, via the augmented reality display system, the indication of the occlusion of a pulmonary vein, the indication of the occlusion of the pulmonary vein further being based at least in part on mesh collision between a subject's anatomical feature virtual mesh and a virtual mesh of the treatment device.

2. The system according to claim 1, wherein:
the virtual organ object is based on a three-dimensional model of the subject's anatomical feature, the subject's anatomical feature including at least one of at least a portion of a heart and at least a portion of vasculature.

3. The system according to claim 1, wherein:

the virtual organ object, the electrogram data associated with the subject's anatomical feature, and the indication of the position of the treatment device, and the real-world environment are simultaneously viewable by the user via the augmented reality display system within a field of view of the user.

4. The system according to claim 1, wherein:

the navigation system is configured to continuously monitor the position of the treatment device within the subject's anatomical feature during a surgical procedure; and the processing circuitry is configured to continuously receive the monitored position from the navigation system and display an indication of the monitored position on the virtual organ object during the surgical procedure.

5. The system according to claim 4, wherein:

the processing circuitry is further configured to continuously update the indication of the monitored position on the virtual organ object during the surgical procedure.

6. The system according to claim 1, wherein:

the navigation system is configured to deliver alternating current to a plurality of external electrodes and orient a plurality of current sources in at least an X plane, a Y plane, and a Z plane for determining the position of the treatment device within the subject's anatomical feature.

7. The system according to claim 1, wherein:

the at least one sensor is further configured to sense an electrical parameter of the heart; and the processing circuitry is configured to display an indication of the electrical parameter via the augmented reality display system.

* * * * *